United States Patent
Destrian et al.

(10) Patent No.: US 10,653,202 B2
(45) Date of Patent: May 19, 2020

(54) SMART AND COMMUNICATING GARMENT ITEM, METHOD AND INSTALLATION FOR BIDIRECTIONAL COMMUNICATION WITH SUCH A GARMENT ITEM

(71) Applicant: INTELLINIUM, Aix en Provence (FR)

(72) Inventors: Mathieu Destrian, Carry-le-Rouet (FR); Giuliano Franchetto, Greasque (FR)

(73) Assignee: INTELLINIUM, Aix En Provence (FR)

( * ) Notice: Subject to any disclaimer, the term of this patent is extended or adjusted under 35 U.S.C. 154(b) by 0 days.

(21) Appl. No.: 16/054,383

(22) Filed: Aug. 3, 2018

(65) Prior Publication Data

US 2018/0338561 A1 Nov. 29, 2018

Related U.S. Application Data

(63) Continuation of application No. PCT/FR2017/050229, filed on Feb. 2, 2017.

(30) Foreign Application Priority Data

Feb. 5, 2016 (FR) ..................................... 16 50956

(51) Int. Cl.
*A43B 3/00* (2006.01)
*A61B 5/00* (2006.01)
(Continued)

(52) U.S. Cl.
CPC ............ *A43B 3/0021* (2013.01); *A43B 3/001* (2013.01); *A61B 5/6807* (2013.01); *G08B 6/00* (2013.01);
(Continued)

(58) Field of Classification Search
CPC ..... A43B 3/0021; A43B 3/001; A61B 5/6807; G08B 6/00; G08B 21/02; G08B 25/10; H04B 1/385
See application file for complete search history.

(56) References Cited

U.S. PATENT DOCUMENTS 7,969,315 B1 6/2011 Ross et al.
2006/0286972 A1* 12/2006 Kates ...................... H04M 1/05
455/415
(Continued)

FOREIGN PATENT DOCUMENTS

EP 2774502 9/2014
FR 2156280 5/1973

OTHER PUBLICATIONS

International Search Report for International Application PCT/FR2017/050229, dated May 12, 2017.

*Primary Examiner* — Mohamed Barakat
(74) *Attorney, Agent, or Firm* — Burris Law, PLLC

(57) ABSTRACT

The present disclosure is directed toward an article of clothing that includes at least one two-way radio communication module able to emit and receive signals, at least one force sensor placed on the article of clothing and configured to detect a stress applied by a wearer to the force sensor, at least one annunciator configured to emit an annunciating signal, a battery, and a digital processing center configured to drive at least one radio communication module to emit a carrier signal, in response to the detection of at least one sequence of successive stresses on said force sensor. The digital processing center drives the annunciator to emit the annunciating signal following the reception of an external signal by the radio communication module or following the detection of at least one sequence of successive stresses on the force sensor.

18 Claims, 5 Drawing Sheets

(51) Int. Cl.
*G08B 6/00* (2006.01)
*G08B 21/02* (2006.01)
*G08B 25/10* (2006.01)
*H04B 1/3827* (2015.01)

(52) U.S. Cl.
CPC ............ *G08B 21/02* (2013.01); *G08B 25/10* (2013.01); *H04B 1/385* (2013.01)

(56) References Cited

U.S. PATENT DOCUMENTS

| | | | |
|---|---|---|---|
| 2014/0135591 A1* | 5/2014 | Jung | A61B 5/0015 |
| | | | 600/301 |
| 2016/0029926 A1* | 2/2016 | Varnum | A61B 5/1036 |
| | | | 73/172 |
| 2016/0249829 A1* | 9/2016 | Trabia | A61B 5/6892 |
| | | | 600/592 |

* cited by examiner

SMART AND COMMUNICATING GARMENT ITEM, METHOD AND INSTALLATION FOR BIDIRECTIONAL COMMUNICATION WITH SUCH A GARMENT ITEM

CROSS-REFERENCE TO RELATED APPLICATIONS

This application is a continuation of International Application No. PCT/FR2017/050229, filed on Feb. 2, 2017, which claims priority to and the benefit of FR 16/50956 filed on Feb. 5, 2016. The disclosures of the above applications are incorporated herein by reference.

FIELD

The present disclosure relates to a garment item enabling a wearer to establish a communication with remote persons, apparatuses or services.

BACKGROUND

The statements in this section merely provide background information related to the present disclosure and may not constitute prior art.

In the field of personal or portable alarm devices, it is known to use portable modules or telephone terminals provided with an alarm button. Such devices have the drawbacks of being little too discrete and bulky, easily forgettable, possibly requiring the use of a telephone terminal or the same to connect to a network, detectable in case of deep-search, and inoperative in some situations (shackled hands, necessity of discretion, etc).

To address some of these problems, it is known from the document EP 2 774 502 to dispose, inside a safety shoe, one or several sensor(s) capable of measuring parameters indicative of a work accident undergone by the wearer of the shoe (such as for example the detection of a fall), a microcontroller (also abstracted as MCU) which determines whether the measured parameters reveal such an accident, and a wireless transceiver capable of automatically transmitting an alarm signal to a remote reader when the microcontroller establishes an accident situation.

However, the shoe of the document EP 2 774 502 does not enable its wearer to notify a danger situation that concerns him or which he is witnessing, but only allows automatically notifying an accident that he has just undergone. In other words, the wearer cannot communicate at his own initiative, because only the automatic determination of an accident situation by the microcontroller on the basis of the measurements of the sensors is at the origin of the communication with the remote reader. In addition, the shoe cannot communicate with the wearer to notify him that his alarm signal (automatic in this instance) has been properly considered, and can neither allow receiving an alert regarding an immediate or incoming danger concerning him. Although audible or luminous warning devices are provided on the shoe, these are activated by the microcontroller only in case of automatic determination of an accident situation, and even in case of dysfunctions of the electronics of the shoe or of discharge of the battery. Thus, the wearer does not receive any confirmation that the alarm signal has been successfully addressed, or that it has been properly received, or that it has been properly taken into consideration by the competent services.

It is also known from the document FR 2 156 280 to equip a shoe with a control member, placed on the sole inside the shoe, which is constituted by a flexible contactor forming a switch which can be manipulated by a toe of the wearer. In case of danger, the wearer displaces the contactor with his toe in order to establish an electrical contact which will automatically trigger the emission of an alarm signal by an emitter housed inside the heel of the shoe.

However, such a shoe does not provide confirmation to the wearer that the alarm signal has been successfully addressed, and still has been properly received, and still is properly taken into consideration by the competent services. In general, this shoe does not allow receiving messages coming from the outside. Besides, the use of a flexible contactor enables only but a binary use, the switch is either open or closed, thereby limiting its use to a simple sending of an alarm signal. Finally, this shoe does not integrate any means for avoiding parasitic, inadvertent or unintentional triggering, in other words false positives, so that, inadvertently, the wearer of the shoe may address an alarm signal in an unintentional manner and without being aware that he has addressed such an alarm signal and without being able to cancel his alarm signal. These and other issues are addressed by the present disclosure.

SUMMARY

In one form, the present disclosure is directed a method for bidirectional communication with a garment item, within an installation comprising a remote central server and at least one gateway for connection between the garment item and the central server. In particular, and without limiting the application, the present disclosure enables a wearer of a garment item to transmit an alarm warning of a danger or crisis situation and, in response to the alarm, receive instructions or information for helping the user in such a situation, and/or to enable a wearer of a garment item to receive an alert notifying a danger or crisis situation, possibly with instructions for managing such a situation.

In another application, the present disclosure can be used for a personal protective equipment which, by definition, includes devices or means intended to be worn or held by a worker in order to protect the wearer against one or several risk(s) likely to threaten his health or his safety, and in particular in the field of safety shoes and even more widely in the field of shoes.

The present disclosure may also be applied to enable interaction or communication for persons with disability, for players of immersive video games, for members of armed forces or police forces needing to establish discrete transmissions without resorting to hands, which are used for other purposes, for members of emergency public utility services such as the fire department, the emergency services, or healthcare services, or for adults practicing private games soliciting the senses.

The present disclosure is directed toward a garment item which provides bidirectional communication between the wearer and at least one external third-party (e.g., a person wearing a similar garment item, an external service via a central server, a communicating connected apparatus, etc). At the initiative of the external third-party or at the initiative of the wearer, the bidirectional communication is activated to exchange messages in an upstream or downstream direction, bearing in mind that such a bidirectional communication will, for example, enable the external third-party to notify the wearer that his message has been properly received and that it is being processed, or still enable the wearer to notify the external third-party that he has properly taken into consideration its message.

The present disclosure also enables the wearer to transmit messages that are more complex than a simple alarm signal, such as predefined coded sequences and/or Morse messages.

A further aspect of the present disclosure is to enable the wearer of the garment item to receive messages coming from other wearers of similar garment items and/or from a computerized system embedded in an object or apparatus and/or from an application available on a portable equipment (telephone, watch, . . . ) and/or from a program available on a local or remote computer server.

To this end, the present disclosure provides a garment item integrating at least one bidirectional radio-communication module configured to emit and receive signals, at least one force sensor placed on the garment item and configured to detect an effort applied by a wearer of the garment item on the at least one force sensor, at least one warning device configured to emit a warning signal at least to the wearer, at least one electric battery, and a reprogrammable and configurable digital processing center which is connected to the at least one radio-communication module, to the at least one force sensor, to the at least one warning device and to the battery. The digital processing center being configured to:

pilot at least one radio-communication module so as to emit a meaningful signal, subsequently to the detection of at least one sequence of successive efforts on said force sensor; and pilot at least one warning device so as to emit a warning signal subsequently to the reception of an external signal by at least one radio-communication module or subsequently to the detection of at least one sequence of successive efforts on said at least one force sensor.

The force sensor, which is a device used to convert a sequence of one or several successive efforts (in this instance a sequence of several successive pushes) applied by the wearer (with a hand, a foot, a finger, a toe, or any other part of the body depending on the type of garment item) on the sensor into a variation of an electrical signal, and in particular into a variation of an electrical resistivity, thereby enables the wearer to emit a more or less complex so-called meaningful signal. The wearer has only to apply on the force sensor a predefined sequence of successive efforts (an effort may be more or less long and/or more or less close in time to the previous effort and to the next effort and/or exerted with a more or less strong pressure) which will be translated by the controller into a meaningful signal associated to a predefined message which will have a meaning for the external services that will receive this meaningful signal. It is also possible to establish a similarly complex communication between the controller of the shoe and the wearer (in particular to request confirmations before alerting the external services).

In order to prevent, and even avoid, false positives, the force sensor(s) are associated to:

an electronic instrumentation based on operational amplifiers; and/or a pre-processing and filtering module for pre-processing and filtering the measurement data originating from the sensor(s), before any analysis by the digital processing center allowing interpreting the sequence of successive efforts performed by the wearer.

Each predefined sequence of successive efforts may correspond to some kind of shortcut for a determined message (for example «alert», «caution! armed men», «special nature incident», «I cannot speak», «I am kidnapped», «I am wounded», «I am attacked», «I am informing you of an danger», «I suspect a person is a terrorist», etc.), or still it may correspond to a sequence in Morse alphabet and/or in any other alphabet or language code which could be configured in the digital processing center. It should be noted that such shortcuts can be parameterized by the wearer and/or by a third-party person (for example a member of the organization supervising the wearer). In addition, as indicated hereinabove, the wearer can perform predefined sequences of successive efforts in Morse alphabet, by acting on the force sensor(s), also in order to emit complex messages.

In addition, the external services can address a message to the wearer of the shoe, in the form of a so-called warning signal, which will be communicated to the wearer via the warning device(s); such a message having a very specific meaning (depending on the selection of the warning device(s) and depending on the form of the warning signal) which will then be interpreted by the wearer, for example meaning «message well received», «sending of the services proceeding», «rendezvous at x location», «call your manager immediately», «quit this area immediately», . . . . It is also conceivable that an external third-party (such as for example a person wearing a similar garment item, an external service, a communicating connected apparatus, . . . ) addresses a complex message which will be translated into a warning signal in Morse alphabet which will be understood by the wearer having knowledge in Morse alphabet.

The warning signals, each having a specific meaning, may be distinguished by tuning the amplitude and/or the magnitude and/or the frequency and/or the pulse widths with a Pulse Width Modulation or PWM.

In the context of the present disclosure, by garment item, is meant an item intended to be worn as a garment by a wearer, such as for example, without limitation, a bust garment (tee-shirt, pullover, jacket, undershirt, polo, tank top, . . . ), an underwear (briefs, shorts, boxer, panties, bra, . . . ), a hands garment (glove, mitten, fingerless glove), a legs garment (trousers, shorts, skirt, . . . ), a feet garment (shoe, sandal, . . . ) or a head garment (hat, bonnet, hood, . . . )

It is also well understood that a bidirectional radio-communication module integrates a transceiver for a communication in an upward direction and in a downward direction.

In one form, the digital processing center integrates at least one microprocessor associated to at least one microcontroller.

Without limitation, the digital processing center integrates at least one FPGA («Field-Programmable Gate Array») component and/or at least one DSP («Digital Signal Processing») component.

Such a solution allows exploiting at least one microprocessor for complex and energy-consuming tasks, and allocating to at least one microcontroller the tasks that consume less energy, those requiring the acquisition of digital or analog external signals and those that can wake up the microprocessor when desired.

The benefit of the microprocessor (MPU)/microcontroller (MCU) duo also lies in the capability of executing several complex programs on the microprocessor which, in turn, has the capability of hosting an advanced operating system.

Besides, this duo enables a decoupled management of the radio-communication modules depending on the consumption of the latter as well as their radio-communication protocol.

For example, the microcontroller will pilot the so-called «connection-less» radio-communication module(s) (for example a radio-communication module under the LoRa™ protocol) and the microprocessor will pilot the so-called «IP» radio-communication module(s) (for example a radio-communication module under the GSM™ or Wi-Fi™ or Li-Fi™ protocol).

According to one feature, the garment item comprises at least one vibrator type warning device placed inside the garment item in order to emit a vibrational warning signal which can be felt by the wearer.

The use of one or several vibrator(s) is particularly advantageous to communicate more or less complex messages, discreetly, to the wearer in the form of vibrational warning signals; each vibrational signal may be in the form of a predefined sequence of successive vibrations (one vibration may be more or less long and/or more or less close in time to the previous vibration and to the next vibration) which will be translated by the wearer as a predefined message having a specific meaning.

Each predefined sequence of successive vibrations may correspond to some kind of shortcut for a given message or still may correspond to a sequence in Morse alphabet and/or in another alphabet or language code which could be configured in the digital processing center. It should be noted that such shortcuts can be parameterized by the wearer and/or by a third-party person.

It should be noted that such vibrational warning signals may be used as vibrational feedbacks (or haptic feedbacks) in the context of the interaction between a program embedded in the digital processing center of the garment item and the wearer, such as for example the confirmation of the execution of a command.

In one form, the garment item comprises several vibrators placed at different spatial positions inside the garment item, in order to emit respective vibrational warning signals which can be felt by different areas of the body of the wearer so as to be spatially interpreted by the wearer.

Due to such spatial distribution of the vibrators inside the garment item, it is possible to address more complex messages to the wearer, and in particular messages for guidance in the space, in order to lead the wearer toward a given destination.

According to another feature, the garment item comprises:
at least one light source type warning device placed outside the garment item in order to emit a luminous warning signal which can be seen (and interpreted) at least by the wearer (and possibly by any person close to the wearer); and/or
at least one sound source type warning device in order to emit an audible warning signal which can be heard (and interpreted) at least by the wearer (and possibly by any person close to the wearer); and/or
at least one odorous source type warning device in order to emit an olfactive warning signal which can be smelt (and interpreted) at least by the wearer (and possibly by any person close to the wearer).

Such warning devices, less discrete than the vibrator(s), allow addressing other messages to the wearer and/or to the possible person(s) nearby, thereby enriching the communication between the wearer and the external third-parties; bearing in mind that such warning devices can be deactivated in some situations notified by the wearer, such as for example a kidnapping situation, the presence of assailants, the presence on a combat area, . . . .

In one form, the digital processing center integrates a first conversion table, in particular a parameterizable type table, configured to convert predefined sequences of successive efforts applied by the wearer on the force sensor into respective meaningful signals associated to messages.

Thus, such a first conversion table allows converting the sequences of successive efforts of the wearer into messages readable by the external third-parties; bearing in mind that the wearer can parameterize this first conversion table beforehand so as to define shortcuts (in other words specific sequences) to address messages of his choice, or to decode sequences of Morse alphabet (in this case, the first conversion table integrates a Morse alphabet table).

It should be noted that to each sequence of successive efforts recognized by the digital processing center in the first conversion table (whether it consists of a shortcut sequence or a Morse alphabet sequence) corresponds a specific meaningful signal. The difference between the different meaningful signals may be achieved in different manners, such as for example and without limitation, by tuning the duration, the amplitude, the frequency, the modulation, . . . .

In one form, the digital processing center integrates a second conversion table, in particular a parameterizable type table, configured to convert predefined external signals into respective emission patterns of at least one warning signal.

Thus, such a second conversion table allows converting the messages addressed by the external services into determined warning signals; bearing in mind that the wearer can parameterize this second conversion table beforehand so as to define shortcuts (in other words specific patterns of warning signals) to understand the messages that are addressed thereto.

In a particular form, the garment item is a shoe comprising a sole and an upper stocking portion provided with an entrance for the introduction of a foot of a wearer.

In one form, the force sensor is positioned on an inner face of the upper stocking portion.

The placement of the at least one force sensor on the upper stocking portion, and not on or inside the sole, allows avoiding false positives (in other words messages made by error), the foot constantly bearing on the sole, guaranteeing sending of meaningful signals intended by the wearer. Such a placement further allows limiting the electrical consumption and limiting the wear of the force sensor over time.

However, in the context of the present disclosure, it is conceivable to integrate the force sensor(s) on or inside the sole.

Preferably, the or each force sensor is positioned on an inner face of the upper stocking portion and at the front of the shoe, so that said or each force sensor is placed above at least one toe of the foot.

Such a localization is particularly advantageous, because at this location (above the toes of the foot), the foot is not in contact with the upper stocking portion, and therefore will not be in contact with the force sensor(s), so that only a vertical push of the toes (or of the hallux alone depending on the lateral positioning) will be able to generate a meaningful signal, thereby avoiding the undesired false signals.

According to a possibility of the shoe, the battery (and its possible charging antenna) are located at the level of the heel of the shoe.

According to another possibility of the shoe, the shoe further comprises a safety shell placed at the front of the shoe, where the or each force sensor is disposed beneath said safety shell.

Thus, the shoe, being a safety shoe, has a shell which will protect the foot toes but also the force sensor which is at the basis of the emission of meaningful signals by the wearer.

In one form, the shoe comprises several vibrators placed respectively at the front, at the top, at the bottom and at the right and left sides of the shoe in order to emit respective vibrational warning signals which can be felt by different areas of the foot.

According to another possibility of the shoe, the sole comprises an external sole layer and an internal sole layer surrounding an insulation layer made of foam, in particular a polyurethane foam, where the digital processing center and the radio-communication module are buried inside said insulation layer.

Thus, the insulation layer will guarantee protection and sealing for the digital processing center and the radio-communication module, and possibly for the battery.

In addition, the shoe may also comprise, connected to the digital processing center, a detector for detecting the presence of the foot inside the shoe, thereby allowing waking up the digital processing center only when a foot is inside the shoe.

It should be noted that such a foot presence detector is distinct from the force sensor used to enable the wearer to perform sequences of successive efforts on the force sensor in order to enable the wearer to communicate messages.

Alternatively or complementarily, the digital processing center, the radio-communication module and possibly the battery may be placed inside a sarcophagus, enabling retrieval and recycling of the electronic components for economic and regulatory reasons.

In a particular form, the antenna(s) associated to the radio-communication module(s) partially comprise the metallic, and in particular ferrous, elements of the shoe (such as for example a safety shell, an anti-perforation metallic blade inserted inside the sole, . . . ).

In a so-called synchronous listening first form, the digital processing center is in a continuous listening phase, during which the digital processing center opens at least one entering communication channel for the reception of any entering message that is addressed thereto from the outside.

In a so-called asynchronous listening second form, the digital processing center switches successively between:

listening phases during which the digital processing center opens at least one entering communication channel for the reception of any entering message that is addressed thereto from the outside;

break phases during which the digital processing center closes its or all its entering communication channel(s).

Thus, whether the listening is synchronous or asynchronous, the digital processing center of the garment item can receive on a regular basis (continuously or with an offset) any entering message, without it being necessary that the wearer of the garment item has previously emitted a message to the outside. In other words, the digital processing center of the garment item can receive on a regular basis any entering message addressed at the initiative of an external emitter (external machine or person), for example to inform him on a specific situation that requires his attention.

In another form of the present disclosure, the garment item comprises a radio-communication module of the long-range radio-communication chip type according to a LPWAN «Low Power Wide Area Network» or LTN «Low Throughput Network» technology.

The use of such a LPWAN or LTN technology, generally used in the field of connected objects (or IoT standing for Internet of Things), has the advantage of enabling a low-consumption communication, with a maximum range comprised between several hundreds of meters up to a few kilometers.

In yet another form, the garment item comprises a radio-communication module of the short-range radio-communication chip type (for example a maximum range comprised between one or five meters, and even fifteen meters) according to a BAN (Body Area Network) or BSN (Body Sensor Network) technology, in order to establish a radio-communication between the shoe and at least one portable device carried by the wearer.

According to one possibility, the portable device is equipped with at least one sensor and/or at least one actuator and/or at least one warning device. Thus, the garment item will be able to communicate with one or several portable device(s) within a BAN network, such portable devices comprising for example at least one sensor monitoring a vital parameter of the body or the environment of the wearer (chemical, thermal, physical, hydrometric, imaging or video environment, . . . ), and/or at least one actuator or warning device (loudspeaker, screen, audio and/or video recorder, . . . ). Thus, the garment item will be able to receive the measurement data from the sensor(s) of this(these) portable device(s) and serve as a gateway for redirecting these measurement data to the external services.

According to another possibility, the portable device is equipped with a short-range radio-identification tag, such as for example a passive RFID tag, an active RFID tag or an NFC chip, where this radio-identification tag stores an identifier and possibly other data. Thus, the garment item will be able to identify the portable device through a short-range control reading. In this manner, it is possible to equip all or part of the portable devices intended to be worn by the wearer of the garment item, such as clothes, tools, protection elements (helmet, glasses, gloves, . . . ), weapons, etc. Then, the garment item will receive through a short-range reading the identifiers from the radio-identification tags of the different portable devices carried by the wearer, and it will thus be possible to check-up whether the wearer has not omitted (or forgotten) to equip himself with either portable device, or whether the wearer carries a non-compliant portable device, or whether the portable device is adapted to the area in which he stands at a given time, or whether the portable device is adapted to at least one predefined instruction, such as a safety instruction, a hygiene instruction, an industrial maintenance instruction or an installation instruction. This verification may be performed either directly by the digital processing center of the garment item, or by a remote server subsequently to the sending of the read identifiers by the digital processing center.

In case of omission of a portable device (because its identifier has not been reported during the control reading), it may be considered to address a warning signal, via at least one warning device, to inform the wearer on this omission.

In case of a non-compliance of a portable device (because its identifier has been reported during the control reading and the verification establishes that its identifier is associated to a non-compliant portable device), it may be considered to address a warning signal, via at least one warning device, to inform the wearer on this non-compliance.

In the case of a portable device which is not adapted to the area in which it is located at a given time or not adapted to at least one predefined instruction, it may be considered to address a warning signal, via at least one warning device, to inform the wearer on this non-compliance.

In a particular form, the garment item comprises a display device (for example a flexible LED screen) piloted by the digital processing center to allow modifying the external patterns of the garment item according to internal events, received messages or any information received by the digital processing center.

It is conceivable that this display device is external to the garment item, yet while being always piloted by the digital processing center of the garment item via a connection established thanks to the radio-communication module.

The present disclosure also relates to an installation for bidirectional communication with at least one wearer of a garment item in accordance with the present disclosure, said installation comprising a remote central server and at least one gateway for connection between a radio-communication module of the garment item and the central server.

In one form, a gateway is in connection with the radio-communication module of the garment item on a LPWAN «Low Power Wide Area Network» or LTN «Low Throughput Network» network, which, recall it, is a low-consumption network.

Afterwards, the gateway is in communication with the central server via a high-speed network with a high or average consumption, such as for example an Ethernet wired network or a 3G, 4G, 5G or Wi-Fi, and even Li-Fi wireless network. Of course, this gateway may also be connected to one or several other similar local similar garment item(s), in other words to several garment items within the reach of the gateway.

According to one possibility, the radio-communication module of the garment item is in connection with the radio-communication module of at least one other garment item in accordance with the present disclosure, either directly or via the gateway.

As example of a direct connection between the radio-communication modules of two garment items, it is conceivable to exploit the radio-communication modules to form a mesh local area network, or Mesh network, by implementing, as a decentralized connection method, a meshing topology where the nodes of the network are the radio-communication modules of the garment items which are connected with at least part of each other in a decentralized manner.

The mesh network enables communication between several wearers of garment items, in particular by bouncing from one node to another, in isolated areas or areas into which the telecommunication networks have difficulty to penetrate. In the mesh network, a radio-communication module may be in direct connection with all or part of the other radio-communication modules, depending on the distances between the wearers.

According to another possibility, the installation further comprises at least one connected apparatus equipped with at least one sensor for measuring a parameter, such as in particular a physical, chemical or environmental parameter, and/or at least one actuator, said connected apparatus further comprising a bidirectional radio-communication module capable of emitting measurement data of its sensor and/or receiving piloting data of its actuator, and wherein the radio-communication module of the garment item is in connection with the radio-communication module of the at least one connected apparatus, either directly or via the gateway.

Thus, the garment item can communicate with this connected apparatus, for example in order to:

receive external signals from this connected apparatus, such as for example an external signal notifying a danger recognized by the apparatus (for example «caution! overheating apparatus», «caution! detection of a gas leakage», . . . ), subsequently to a measurement by its sensor of a parameter beyond or below a given threshold; and/or transmit a meaningful signal which will form a piloting signal received by the connected apparatus and triggering its actuator, such as for example a door opening, an activation of an aspiration, an activation of a siren, etc.

According to another possibility, the installation further comprises at least one portable device carried by the wearer of the garment item, said portable device integrating:

at least one sensor for measuring a parameter, such as in particular a mechanical, physical, chemical, environmental or physiological parameter, and/or at least one actuator or warning device, such as in particular an audio and/or video recording unit, a sound source, an odorous source, a vibrational source, a visual emitter such as a screen;

said portable device further integrating at least one short-range radio-communication chip according to a WBAN «Wireless Body Area Network» or WBASN «Wireless Body Area Sensor Network» technology, and wherein said short-range radio-communication chip of the portable device is in connection with the short-range radio-communication chip of the garment item.

In this manner, the digital processing center of the garment item can retrieve data coming from the portable device, and can transfer these data to an external third-party (the garment item thus operating as a transfer gateway) and/or can analyze them in order to emit warning signals to the wearer.

The present disclosure also concerns a method for bidirectional communication with a garment item in accordance with the present disclosure, comprising the following steps:

detection of a sequence of successive efforts performed by a wearer of the garment item on the at least one force sensor;

reception by the digital processing center of a detection signal of said sequence of successive efforts by the at least one force sensor, after a possible pre-processing and filtering of the signals originating directly from the at least one force sensor;

analysis by the digital processing center of said detection signal in order to check up whether it is associated to a predefined meaningful signal corresponding to an intelligible message;

piloting by the digital processing center of at least one warning device so as to emit a warning signal subsequently to the reception of said detection signal;

piloting by the digital processing center of the radio-communication module so as to emit said meaningful signal;

reception of an external signal by the radio-communication module, and transmission of said external signal to the digital processing center;

piloting by the digital processing center of at least one warning device so as to emit a warning signal subsequently to the reception of said external signal.

In a synchronous listening first form, the digital processing center is in a continuous listening phase, during which the digital processing center opens at least one entering communication channel for the reception of any entering message that is addressed thereto from the outside.

In an asynchronous listening second form, in the context of the bidirectional communication method, the digital processing center switches successively between:

listening phases during which the digital processing center opens at least one entering communication channel for the reception of any entering message that is addressed thereto from the outside;

break phases during which the digital processing center closes its or all its entering communication channel(s).

According to one possibility, whether the listening is synchronous or asynchronous, this bidirectional communication method comprises the following successive steps:

during the or a listening phase, the digital processing center receives the announcement message coming from an external emitter;

the digital processing center pilots at least one warning device, in order to generate a specific emission announcement pattern of at least one warning signal;

the digital processing center receives a detection signal originating from the at least one force sensor subsequently to the completion, by the wearer of the garment item, of a sequence of successive efforts on the at least one force sensor and which corresponds to a receipt-acknowledgement haptic sequence;

the digital processing center converts the detection signal into a receipt-acknowledgement message;

the digital processing center communicates the receipt-acknowledgement message to the external emitter.

Thus, the external emitter, which has taken the initiative of addressing an announcement message to the garment item, and more specifically to its wearer, will receive a receipt-acknowledgement message which will confirm him that the wearer has properly received (and understood) the announcement message.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
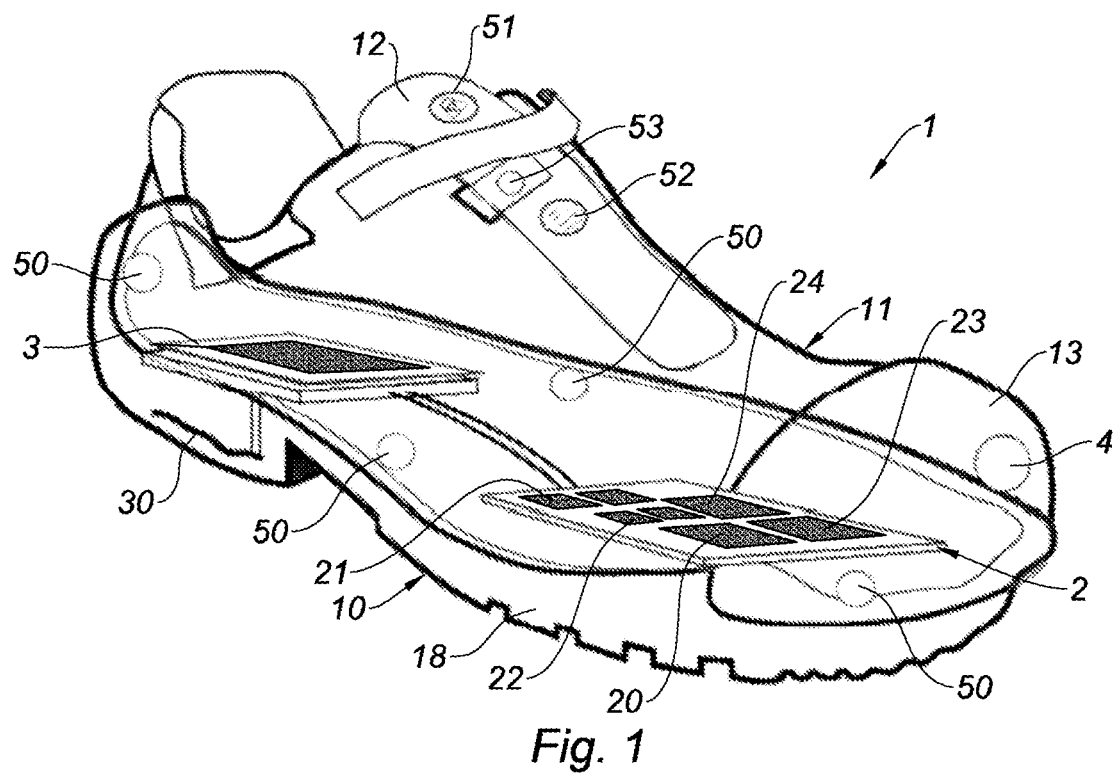
FIG. 1 is a partially transparent perspective view of a shoe-type garment item in accordance with the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The following detailed description concerns a shoe-type garment item 1 in accordance with the present disclosure, intended to be worn at the foot by a wearer. The present disclosure is not limited to such a shoe, but may be considered with other garment items (e.g., bust garments, hands garment, underwear, head garment, etc), that is to say that the different electronic components described hereinafter may be integrated to another type of garment item, and not only to the shoe 1 described hereinafter.

Referring to FIG. 1, the shoe 1, in accordance with the present disclosure comprises, a sole 10 and an upper stocking portion 11 (also called rod) provided with an entrance for the introduction of a foot of a wearer, possibly as well as a tongue 12 placed on top of the upper stocking portion 11 and in particular beneath a lacing or more generally tightening area of the shoe 1.

The sole 10 comprises an external sole layer 18 (which comes into contact with the ground) and an internal sole layer (not illustrated, which is in contact with the foot), as well as an insulation layer (not illustrated) interposed between the external sole layer 18 and the internal sole layer. In particular, this insulation layer is made of foam, such as a polyurethane foam.

In one form, the shoe 1 illustrated in FIG. 1 is a safety shoe, categorized in personal protective equipment, and integrates as such a safety shell 13 placed at the front of the shoe 1, and more specifically inside the upper stocking portion 11, in order to protect the toes of the foot. For example, this safety shell 13 is made of a metallic material, a composite material or a plastic material.

The shoe 1 internally integrates an electronic board 2 placed inside the sole 10, and more specifically buried inside its insulation layer, in particular at the front of the shoe 1. Alternatively, the electronic board 2 may be placed substantially at the middle of the sole 10, and still at the level of the foot arch, in particular at the level of the setback between the heel and the plate of the sole.

The electronic board 2 integrates a reprogrammable and configurable digital processing center 20, which comprises a microprocessor (also abstracted as MPU or electronic microprocessor or digital signal processor), and/or a microcontroller (also abstracted as MCU). The electronic board 2 also integrates at least one random-access memory 21 (or RAM memory) and at least one Flash memory 22 connected to the digital processing center 20.

The electronic board 2 integrates a pre-processing and filtering module, in this instance a hardware module, which allows pre-processing and filtering the measurement data originating from the force sensor(s) 4 described later on.

The electronic board 2 integrates a bidirectional radio-communication module 23 capable of wirelessly emitting and receiving signals, where this radio-communication module 23 is of the long-range radio-communication chip type according to a LPWAN «Low Power Wide Area Network» or LTN «Low Throughput Network» technology.

As a non-limiting example, among the different LPWAN or LTN technology protocols, mention may be made to the LoRa™, Sigfox™, NWave™, Neul™, OnRamP™, 5G™, Platanus™, Telensa™ and Weightless™ protocols.

The long-range radio-communication chip 23 is connected to the digital processing center 20, and more specifically to the microprocessor that pilots it, as well as to an antenna (not illustrated) disposed within the shoe 1.

The electronic board 2 also integrates another bidirectional radio-communication module 24 of the short-range radio-communication chip type according to a WBAN «Wireless Body Area Network» or WBASN «Wireless Body Area Sensor Network» technology, in order to allow establishing a radio-communication on a WBAN or WBASN network between the shoe 1 and a mobile terminal 65 and/or at least one portable device 66 (shown in FIG. 2) carried by the wearer and equipped with at least one sensor.

As a non-limiting example, among the different WBAN or WBASN technology protocols, mention may be made to the Zigbee™ and Bluetooth™ Low Energy (BLE) protocols, as well as to the IEEE 802.15 standards including the IEEE 802.15.4 and IEEE 802.15.6 standards, as well as to an RFID (radio frequency identification) or NFC (Near Field Communication) protocol.

It is conceivable that the shoe 1 also integrates a long-range radio-communication chip such as a GSM radio-communication chip, which may be used only in case of absence of communication with the other radio-communication modules, and in case of some situations, because of the high energy consumption of such a GSM chip.

It should be noted that the aforementioned different electronic components may also be in the form of one single or several SiP (System-in-package) or SoC (System-on-Chip) component(s).

The shoe 1 internally integrates an electric power supply battery 3 placed inside the sole 10, and more specifically buried inside its insulation layer, in particular at the level of the heel. The battery 3 is connected to the electronic board 2, and in particular to the digital processing center 20 which manages the battery 3 so as to power the different electronic components of the shoe 1. It is also conceivable to provide for a management module of the battery 3 which is external to the digital processing center.

Preferably, the battery 3 is rechargeable, either in a wired manner (an external socket then being provided on the shoe 1), or in a contactless manner, for example according to an inductive technology such as the Qi technology, or by means of an energy harvesting system which converts movements of the human body (and in particular walking or running movements) into electrical energy.

Alternatively, the battery 3 is not rechargeable and should therefore be replaced when empty via a hatch provided in the sole 10, and in particular in the heel.

In the example of FIG. 1, the battery 3 is rechargeable in a contactless manner with an inductive technology, so that the battery 3 is connected to at least one antenna or coil 30 placed inside the sole 10. Thus, charging of the battery 3 is performed by placing the shoe 1 proximate to or over an inductive charging emitter station (not illustrated), this charging emitter station including at least one primary induction coil capable of generating a charging induced current into the at least one coil 30 by mutual induction.

The shoe 1 internally integrates at least one force sensor 4, such as a piezoelectric sensor or transducer, which is disposed on an inner face of the upper stocking portion 11, inside the shoe 1, in order to allow detecting an effort applied by the foot on the force sensor 4; such an effort (or pressure) applied by the foot on the force sensor 4 resulting in a variation of the electrical resistivity within the force sensor 4.

The or each force sensor 4 is connected to the pre-processing or filtering module of the electronic board 2, in order to pre-process and filter the measurement data (variations of the resistivity) of this force sensor 4, and then this pre-processing and filtering module addresses a pre-processed and filtered signal to the digital processing center 20, and more specifically to the microprocessor, in order to process it as described later on. The or each force sensor 4 is electrically powered by the battery 3 via the digital processing center 20.

The or each force sensor 4 is placed at the front of the shoe 1, above the toes of the foot, and in particular on the internal side of the shoe 1 so as to be above the hallux of the foot. Conventionally, and in particular in safety shoes, the toes of the foot are not in compressive contact with the upper stocking portion 11, so that the toes of the foot may be in slight contact with the force sensor 4 in normal condition, and even not be in contact at all, and only an intentional movement by the wearer (who raises his hallux or all his toes) will ensure a detection of the effort applied on the force sensor(s) 4. In the case of a safety-type shoe 1 with a safety shell 13, the or each force sensor 4 is disposed beneath this safety shell 13.

A prior calibration of the or each force sensor 4 and/or the selection of a minimum detection threshold may be provided so as to avoid that too weak contacts of the foot on the force sensor(s) 4 (for example when walking) be perceived as intentional efforts of the wearer for transmitting a message (also called false positives).

In order to reduce as much as possible the false positives (and therefore save the battery 3 and avoid erroneous solicitations of the external services), there is provided the pre-processing and filtering module which constitutes a shaping electronic device receiving at input the measurement data from the corresponding force sensor 4 (in this instance the variation of the electrical resistivity), and generating at output a pre-processed and filtered, in other words shaped, signal, intended to the digital processing center 20, such a pre-processing and filtering module may for example be a two-threshold comparator or a hysteresis flip-flop circuit, such as a Schmitt Trigger.

The shoe 1 internally integrates several vibrator type warning devices 50 placed inside the shoe 1, and in particular placed on the inner face of the upper stocking portion 11, each intended to emit a vibrational warning signal (also called haptic signal) which can be felt by the foot. These vibrators 50 are connected to the digital processing center 20, and in particular to the microcontroller, which pilots them independently of each other, and they are electrically powered by the battery 3 via the digital processing center 20.

As shown in FIG. 1, the vibrators 50 are placed respectively at the front (at the level of the toes), at the rear (at the level of the heel) and at the sides (to the right and to the left) of the shoe 1 in order to emit respective vibrational warning signals which can be felt by different areas of the foot (toe(s), heel, internal and external sides). Thus, these different vibrators 50 enable a two-dimensional geospatial meshing (front, rear, right and left).

It is also conceivable to provide a vibrator placed inside the sole 10 beneath the foot and another vibrator placed above the foot (for example in the tongue 12), thereby enabling a three-dimensional geospatial meshing (front, rear, right, left, top and down).

Optionally, the shoe 1 also integrates other warning devices capable of emitting warning signals to the wearer, such as for example:

a light source type warning device 51 placed on the outside of the shoe 1 in order to emit a luminous warning signal which can be seen by the wearer, this light source 51 may for example be placed on top of the tongue 12 and consist of an RGB light-emitting diode allowing for different colors of the light; and/or a sound source type warning device 52 in order to emit an audible warning signal which can be heard by the wearer, this sound source 52 may for example be placed on top of the tongue 12 and consist of a buzzer or beeper (for emitting a simple audible signal) or of a loudspeaker (for emitting vocal signals); and/or an odorous source type warning device (not illustrates) in order to emit an olfactive warning signal which can be smelt by the wearer.

These warning devices 51, 52 are connected to the digital processing center 20 which pilots them independently of each other, and they are electrically powered by the battery 3 via the digital processing center 20.

Optionally, the shoe 1 also integrates a detector (not illustrated) for detecting the presence of the foot inside the shoe 1. This presence detector may be a magnetic loop sensor, a photodetector or a luminous flux sensor, an electromechanical sensor, etc. This presence detector is connected to the digital processing center 20 which thus receives the information on the presence or on the absence of the foot in the shoe 1.

Optionally, the shoe 1 integrates one or several button(s) 53 connected to the digital processing center 2, and which may be manually triggered by the wearer for different uses (pairing, manual sending of an alert, reset of the digital processing center, etc.).

It is also conceivable to integrate sensors to the shoe 1, such as for example one or several sensor(s) selected in the following list: accelerometer, orientation sensor, gyroscope, magnetometer, humidity sensor, temperature sensor, sensor of the pressure of the foot on the sole, gas sensor (in particular ink-based gas sensor comprising nanoparticles having detection properties), image sensor (photographic camera or video camera). Of course, this or these sensor(s) will be connected to the digital processing center 20 which will receive the corresponding measurement data.

By having the vibrators 50, the force sensor(s) 4 and the long-range radio-communication chip 23, all of them being connected to the digital processing center 20, the shoe 1 enables the wearer to communicate in a bidirectional manner with external services (e.g., member of his team, direct supervisor, safety officer, safety public utility service, etc). Because the digital processing center 20 is, on the one hand, capable of piloting the long-range radio-communication chip 23 to emit a message (called meaningful signal) subsequently to the detection of a sequence of successive efforts on the force sensor 4 and, on the other hand, capable of piloting the warning devices 50, 51, 52 to emit a warning signal subsequently to the reception of an external signal by the long-range radio-communication chip 23; so that:

the wearer can emit more or less complex messages by exerting sequences of successive efforts on the force sensor 4 which will be translated by the digital processing center 20 into intelligible messages (called meaningful signals) which will be wirelessly transmitted by the long-range radio-communication chip 23;

the wearer can receive more or less complex messages (called external signals) received by the long-range radio-communication chip 23, which will be converted by the digital processing center 20 into emission patterns of at least one warning signal (vibrational signal and/or luminous signal and/or audible signal and/or olfactive signal) emitted by the concerned warning devices 50, 51, 52.

In one form, for a communication from the external services to the wearer, only the vibrators 50 may be activated in order to transmit vibrational sequences (haptic sequences) comprising successive vibrations understandable by the wearer, by tuning the magnitude of the vibrations, the duration of the vibrations, the time interval between the vibrations, the selection of the activated vibrators 50 among the vibrators at the front, at the rear, at the right, at the left and possibly at the top and at the bottom.

On this dual basis, the digital processing center 20 integrates:

a first conversion table configured to convert predefined sequences of successive efforts applied by the foot on the force sensor 4 into respective meaningful signals associated to messages contextual or intelligible by the external services;

a second conversion table configured to convert predefined external signals (coming from the external services) into respective emission patterns of at least one warning signal.

These conversion tables may be parameterizable so that the wear could define shortcuts for the sequences of successive efforts applied by the foot on the force sensor 4 and shortcuts for the emission patterns of at least one warning signal.

In order to reduce as much as possible the false positives, it is provided that:

with the pre-processing and filtering module, a software pre-processing and filtering of the signal coming from the or each force sensor 4, on the basis of a sequence with a minimum and maximum duration (in other words, this pre-processing and filtering module checks up whether the duration of the signal is comprised within a given time frame); and with the digital processing center 20, and more specifically with the microprocessor, a processing of the signal coming from the pre-processing and filtering module, consisting in comparing the latter with sequences recorded in the first conversion table.

It should be noted at least one benefit of associating, for the digital processing center 20, at least one microprocessor (in particular a microprocessor integrating a hardware memory management unit or MMU, standing for «Memory Management Unit») and at least one microcontroller, so that the microprocessor performs the complex digital treatments consuming much electrical energy (in particular the processing and sending of the data originating from the force sensor(s) 4 and the piloting of the warning devices) and the microcontroller performs the simple tasks consuming little electrical energy (in particular the reception of data coming from the external sensors).

It should also be noted that the shoe 1 of the right foot (respectively of the left foot) of a wearer can communicate with the shoe of the left foot (respectively of the right foot)

of the same wearer, in order to distribute between the two shoes 1 part of the digital processing center 20 (for example the microprocessor in the right shoe and the microcontroller in the left shoe, or vice versa, or still a radio-communication module type in the right shoe and another radio-communication type in the left shoe), thereby enabling a distribution of the electronic resources and therefore of the weight between the two shoes.

Figure 2:
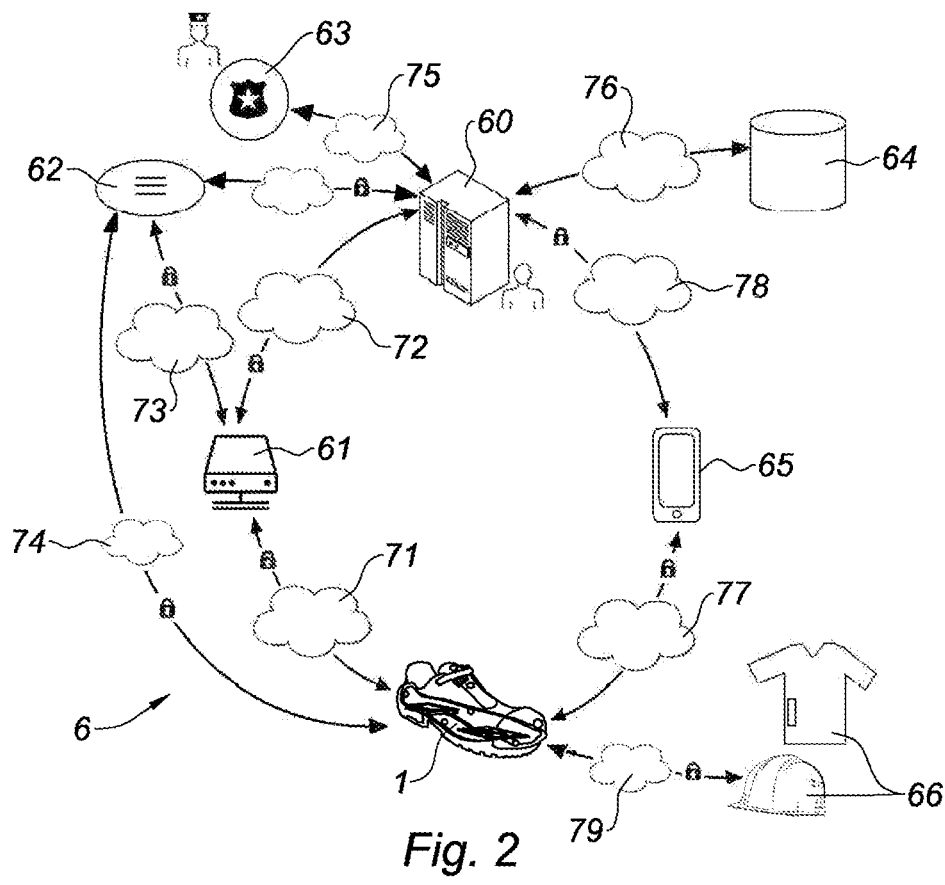
FIG. 2 is a schematic of an installation for bidirectional communication with the shoe of FIG. 1.

Referring to FIG. 2, the shoe 1 integrates into a bidirectional communication installation 6 comprising at least one such a shoe 1, as well as a remote central server 60 and a gateway 61 for connection between the shoe 1 and the central server 60.

The gateway 61, such as a gateway or nano-server, is in connection with:

the long-range radio-communication chip 23 of the shoe 1 on a LPWAN or LTN 71 network; and the central server 60 via a high-speed network 72 with a high or average consumption, such as for example an Ethernet wired network or a 3G, 4G, 5G or Wi-Fi, and even Li-Fi wireless network.

The installation 6 may also comprise one or several connected apparatus(es) 62, where the or each connected apparatus 62 is equipped with:

at least one sensor for measuring a parameter (such as for example a physical, chemical, environmental parameter or a state parameter of a machine) and/or at least one actuator; and a bidirectional radio-communication module capable of emitting measurement data of its sensor and/or receiving piloting data of its actuator.

The radio-communication module of the connected apparatus 62 is in connection with the gateway 61 via a high-speed network 73 with a high or average consumption, such as for example an Ethernet wired network or a 3G, 4G, 5G or Wi-Fi, and even Li-Fi wireless network, so that the connected apparatus 62 is in connection with the shoe 1 via the gateway 61.

The connected apparatus 62 may also be in direct connection with the shoe 1 via a LPWAN or LTN 74 network, provided that the connected apparatus 62 integrates an adapted long-range radio-communication chip, and provided that the shoe 1 is within the reach of the connected apparatus 62 in this LPWAN or LTN 74 network.

The central server 60 may also be connected to a public utility service server 63 (such as a for example the police, the army, the fire department, the emergency services, etc) via a high-speed network 75 with a high or average consumption, such as an Ethernet wired network or a 3G, 4G, 5G or Wi-Fi, and even Li-Fi wireless network.

The central server 60 may also be connected to a client server 64 (accessible for example by a company which wishes to exchange with its employees in the field) via a high-speed network 76 with a high or average consumption, such as for example an Ethernet wired network or a 3G, 4G, 5G or Wi-Fi, and even Li-Fi wireless network.

The shoe 1 may also be connected to a radio-communication mobile terminal 65 (such as a smartphone-type telephone terminal, a digital tablet or a personal digital assistant (PDA)) via a WBAN or WBASN 77 network (or via an NFC short-range connection which involves the presence of an NFC chip inside the shoe 1); this mobile terminal 65 being as such provided with a short-range radio-communication chip according to the WBAN or WBASN technology (and yet still an NFC chip). Furthermore, this mobile terminal 65 may, in turn, be connected to the central server 60 via a high-speed wireless network 78, such as for example a 3G, 4G, 5G or Wi-Fi, and even Li-Fi network.

For example, the mobile terminal 65 may serve in parameterizing the conversion tables used by the digital processing center 20 of the shoe 1, in receiving information from the digital processing center 20 on the status of the different electronic components which equip the shoe 1.

The shoe 1 may also be connected to a portable device 66 (such as a garment, a helmet, a bracelet, a weapon, a tool, etc.) carried by the wearer of the shoe 1, via a WBAN or WBASN network 79; this portable device 66 being as such provided with a short-range radio-communication chip according to the WBAN or WBASN technology.

This portable device 66 may integrate at least one sensor for measuring a parameter, such as:

a physical parameter (e.g., acceleration, displacement, orientation, speed);

a chemical parameter (e.g., detection of a gas);

an environmental parameter (e.g., ambient humidity, ambient temperature);

a physiological parameter (e.g., glycemia, arterial pressure, electrocardiogram, encephalogram, electromyogram, oximetry, transpiration).

Thus, the digital processing center 20 of the shoe 1 can receive measurement data coming from the sensor(s) of the portable device 66, in order to follow them to the central server 60 (the shoe then serving as a gateway) or to process them (for example by comparison with a minimum threshold and/or a maximum threshold) before generating afterwards an alert signal to the central server 60.

Alternatively or complementarily, this portable device 66 may integrate a short-range radio-identification tag (for example a passive RFID tag, an active RFID tag, or an NFC chip) storing an identifier and possibly other data. Thus, the digital processing center 20 of the shoe 1 can receive the identifiers of the portable devices 66, in order to follow them to the central server 60 for processing (the shoe then serving as a gateway) or to process them on its own, before generating afterwards a warning signal to the wearer, so as to notify him that he has omitted or forgotten to equip himself with either portable device and/or that a portable device is not compliant and/or that a portable device is not adapted to the area in which he stands at a given time or not adapted to at least one predefined instruction (for example a safety instruction, a hygiene instruction, an industrial maintenance instruction or an installation instruction).

Moreover, although it is not illustrated in FIG. 2, the shoe 1 may be in direct connection with another shoe 1 (that is to say a shoe 1 worn by another wearer) via a LPWAN or LTN network, provided that the other shoe 1 is within the reach of the shoe 1 in this LPWAN or LTN network. In this respect, the radio-communication modules 23 of several shoes 1 may form a mesh local area network, or Mesh network, by implementing a meshing topology where the nodes of the network are the radio-communication modules 23 which are connected with at least part of each other in a decentralized manner.

It is also conceivable that the shoe 1 is in connection with another shoe 1 via the gateway 61.

In addition, the digital processing center 20 can receive data from detectors inside the shoe 1 which will be analyzed so that, under some predefined conditions associated to the measurement data of the or each detector, the digital processing center 20 activates at least one warning device 50, 51, 52 to warn the wearer about a danger with regards to these predefined conditions, without requiring any radio-communication with an external third-party. For example, the detector is a geolocalization device (for example a GPS system) or a proximity detector (for example an RFID technology detector) placed in the shoe 1 and the predefined conditions correspond to a geolocalization or a presence detection in a danger area.

The following description concerns a method for bidirectional communication with a shoe 1, within an installation 6, such a method comprising different phases of communication between the different components of the installation 6.

In all the communication phases listed below, the communication takes place between the first wearer whose foot P is in a first shoe 1, the digital processing center 20 of the first shoe 1, and one or several external third-party(ies) or actor(s) of the installation 6.

Figure 3:
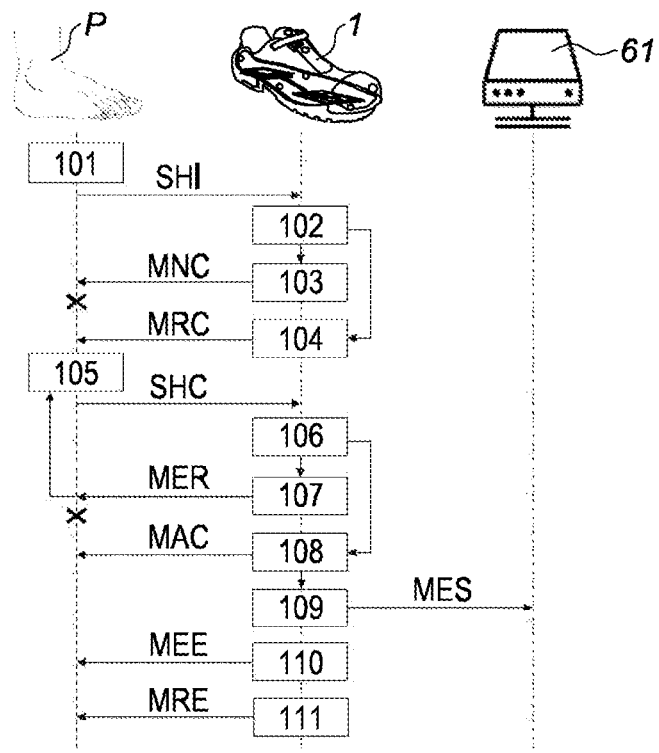
FIG. 3 is a flowchart of a first phase of communication between a first shoe and a first gateway in accordance with the present disclosure.

For example, referring to FIG. 3, a first communication phase may be established between a first wearer whose foot P is in a first shoe 1, the digital processing center 20 of the first shoe 1 and one or several gateway(s) 61.

For clarity reasons, each communication phase listed below concerns the communication between the first wearer whose foot P is in a first shoe 1, the digital processing center 20 of the first shoe, and a unique actor of the installation 6, but it goes with saying that the communication phases may be established in parallel so as to enable the communication of the first wearer with several actors of the installation 1.

Referring to FIG. 3, a first phase of communication between a first wearer whose foot P is in a first shoe 1, the first shoe 1 and a first gateway 61 is described hereinafter.

At a first step 101, the first wearer performs with his foot P a sequence of successive efforts on the force sensor(s) 4 in order to communicate a message (such as an alert message), this sequence of successive efforts being called initial haptic sequence SHI and being received by the shoe 1 (and more specifically received by the force sensor(s)). The initial haptic sequence SHI may consist of an alert message haptic sequence SHA (in order to notify an alert) or of a message haptic sequence SHM (in order to address a message, this sequence may be a message shortcut sequence or a message sequence in Morse alphabet and/or in another alphabet or language code which may be configured in the digital processing center 20).

At a second step 102, the digital processing center 20 of the first shoe 1 receives a detection signal SDI of the initial haptic sequence SHI (after pre-processing and filtering of the measurement data of the force sensor(s) 4), and this digital processing center 20 analyzes this detection signal SDI and looks up whether the later corresponds to a predefined (or preconfigured) sequence present in the first conversion table; bearing in mind that the sequences recorded in the first conversion table form shortcuts for intelligible messages.

If the digital processing center 20 does not recognize the detection signal SDI as corresponding to a predefined sequence, then, at a third step 103, the digital processing center 20 pilots at least one warning device 50, 51, 52 (and in particular only one or several vibrator(s) 50 for discretion), in order to generate a specific emission pattern of at least one warning signal, called non-understanding pattern MNC, which will be understood by the first wearer as meaning that the first shoe 1 has not understood his initial haptic sequence SHI.

If the digital processing center 20 does not recognize the detection signal SDI as corresponding to a predefined sequence SEQ, then, at a fourth step 104, the digital processing center 20 pilots at least one warning device 50, 51, 52, in order to generate a specific emission pattern of at least one warning signal, called recognition pattern MRC, which will be understood by the first wearer as meaning that the first shoe 1 has understood its initial haptic sequence SHI.

Afterwards, at a fifth step 105, the first wearer having understood that his initial haptic sequence SHI has been understood or recognized by the digital processing center 20, he must confirm his request by repeating the same initial haptic sequence SHI, if this initial haptic sequence SHI consists of an alert message haptic sequence SHA, in order to limit false positives. Thus, at the fifth step 105, the first wearer performs with his foot P a confirmation haptic sequence SHC which must be identical to the initial haptic sequence SHI, and this in the case where he wishes to emit an alert message.

In the case where the first wearer wishes to transmit an informative message having no alarming nature, he would carry out at the first step an initial haptic sequence SHI consisting of a message haptic sequence SHM for notifying the digital processing center 20 that he intends to emit an informative message. At the fifth step, the first wearer having understood that his initial haptic sequence SHI has been understood or recognized by the digital processing center 20, he does not have to confirm his request, and can then perform with his foot P an informative message free haptic sequence in the form of a pre-recorded message shortcut or of a sequence in Morse alphabet and/or in another alphabet or language code.

There may be provided a maximum time for this fifth step, in other words the first wearer has a maximum time to confirm his request (or to carry out his informative message free haptic sequence), otherwise the digital processing center 20 cancels the consideration of the initial haptic sequence SHI. It is also conceivable that, if this maximum time is surpassed, the digital processing center 20 pilots at least one warning device 50, 51, 52, in order to generate a specific emission pattern of at least one warning signal, called error pattern MER, which will be understood by the first wearer as meaning that no haptic sequence has been detected within the allocated time and that the communication phase stops at that point.

At a sixth step 106, the digital processing center 20 receives a detection signal SDC of the confirmation haptic sequence SHC (after pre-processing and filtering of the measurement data of the force sensor(s) 4), in the case where the initial haptic sequence SHI consists of an alert message haptic sequence SHA, and compares it with the predefined sequence SEQ associated to the initial haptic sequence SHI.

If the initial haptic sequence SHI consists of a message haptic sequence SHM then, at this sixth step 106, the digital processing center 20 receives a detection signal SDC of the informative message free sequence (after pre-processing and filtering of the measurement data of the force sensor(s) 4), and decodes it with its first conversion table which integrates the message shortcuts, as well as the Morse alphabet and/or another alphabet or language code.

If the digital processing center 20 does not recognize the detection signal SDC as corresponding to the sequence SEQ or as corresponding to an informative message sequence (according to a pre-recorded shortcut or according to a pre-recorded alphabet), then, at a seventh step 107, the digital processing center 20 pilots at least one warning device 50, 51, 52, in order to generate a specific emission pattern of at least one warning signal, called error pattern MER, which will be understood by the first wearer as meaning that the confirmation haptic sequence SHC is different from the initial haptic sequence SHI or has not been understood, and that his request has not therefore been processed. In one form, the first wearer has at least one other possibility to repeat a confirmation haptic sequence SHC which is identical to the initial haptic sequence SHI, or to repeat an informative message free haptic sequence, again with a maximum time for execution.

If this maximum time is surpassed, the digital processing center 20 pilots at least one warning device 50, 51, 52, in order to generate a specific emission pattern of at least one warning signal, called error pattern MER, which will be understood by the first wearer as meaning that no detection sequence SDC has been received within the allocated time and that the communication phase stops at that point.

If the digital processing center 20 recognizes that the detection signal SDC corresponds to the sequence SEQ or to an informative message sequence, then, at an eighth step 108, the digital processing center 20 pilots at least one warning device 50, 51, 52, in order to generate a specific emission pattern of at least one warning signal, called approval pattern MAC, which will be understood by the first wearer as meaning that the confirmation haptic sequence SHC is identical to the initial haptic sequence SHI (in the case where the initial haptic sequence SHI consists of an alert message haptic sequence SHA) or has been properly understood (in the case where the initial haptic sequence SHI consists of a message haptic sequence SHM), and that his request will therefore be processed and sent by the first shoe 1 to one or several external third-party(ies), actor(s) of the installation 6 illustrated in FIG. 2.

At a ninth step, the digital processing center 20 sends to the first gateway 61 (which is within reach on the LPWAN or LTN network) a message MES associated to the sequence SEQ in the first conversion table, in other words associated to the initial haptic sequence SHI, or still associated to the informative message free haptic sequence.

In the case of a failure in sending of the message MES, then, at a tenth step 110, the digital processing center 20 pilots at least one warning device 50, 51, 52, in order to generate a specific emission pattern of at least one warning signal, called sending failure pattern MEE, which will be understood by the first wearer as meaning that the first shoe 1 fails in sending the message. By default, sending of the message MES has priority for the digital processing center 20, so that the digital processing center 20 tries indefinitely to send the message MES and, depending on the selected configuration, the sending failure pattern MEE is implemented at regular intervals to inform the first wearer that the message MES has not yet been sent.

In case of success in sending the message MES, then, at an eleventh step 111, the digital processing center 20 pilots at least one warning device 50, 51, 52, in order to generate a specific emission pattern of at least one warning signal, called sending success pattern MRE, which will be understood by the first wearer as meaning that the shoe 1 has succeeded in sending the message.

Figure 4:
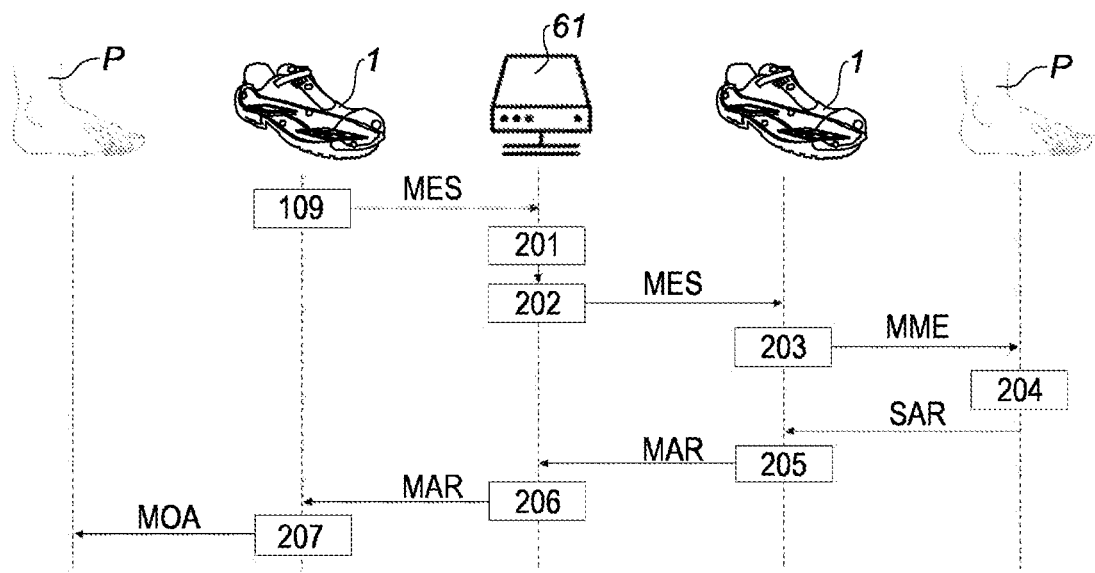
FIG. 4 is a flowchart of a second phase of communication, which follows the first phase of FIG. 3, between the first shoe and a local second shoe via the first gateway in accordance with the present disclosure.

Referring to FIG. 4, a second communication phase, which follows the first communication phase described hereinabove with reference to FIG. 3, consists of a communication between the first wearer whose foot P is in the first shoe 1, the first shoe 1, the first gateway 61, a second wearer whose foot P is in a second shoe 1 and the second shoe 1, and is described hereinafter. In this second phase, the second shoe 1 is within the reach of the first gateway 61 on the LPWAN or LTN network.

After reception of the message MES coming from the first shoe 1, at a first step 201, the first gateway 61 checks up thanks to a local database whether other shoes 1 (and therefore other wearers) are within reach for receiving the message MES, thereby enabling a more rapid processing time of the request, since there is no need to pass through the central server 60.

At a second step 202, the first gateway 61 having detected a second shoe 1 within reach, it redirects the message MES to the second shoe 1 within reach.

At a third step 203, after reception of the message MES, the digital processing center 20 of the second shoe 1 pilots at least one warning device 50, 51, 52, in order to generate a specific emission pattern of at least one warning signal, called message pattern MME, which will be understood by the second wearer by associating it to the message MES addressed by the first wearer. In other words, the second wearer receives this message pattern MME in his second shoe 1, and knows how to translate it into an intelligible request or information.

In order to attract the attention of the second wearer, the message pattern MME may be preceded by a wake-up pattern (for example a long vibration followed by a break) so that the second wearer could concentrate on the message pattern MME that follows.

At a fourth step 204, the second wearer, having understood the request of the first wearer, confirms the proper reception and the proper understanding of the message pattern MME by performing with his foot P a sequence of successive efforts on the force sensor(s) 4 which corresponds to a receipt-acknowledgement haptic sequence SAR to notify the proper consideration of the request of the first wearer. As long as the second wearer has not performed the receipt-acknowledgement haptic sequence SAR, the message pattern MME is repeated at regular intervals on his second shoe 1. It should be noted that this receipt-acknowledgement haptic sequence SAR may also contain a specific sub-sequence SSI relating to instructions and/or information intended to the first wearer.

At a fifth step 205, the digital processing center 20 of the second shoe 1 receives a detection signal SDAR of the receipt-acknowledgement haptic sequence SAR (after pre-processing and filtering of the measurement data of the force sensor(s) 4), and converts it into a receipt-acknowledgement message MAR, before transmitting it to the first gateway 61. In the case of a sub-sequence SSI, the receipt-acknowledgement message MAR will contain instructions and/or information intended to the first wearer.

At a sixth step 206, the first gateway 61 redirects the receipt-acknowledgement message MAR to the first shoe 1 within reach.

At a seventh step 207, the digital processing center 20 of the first shoe 1 receives the receipt-acknowledgement message MAR and then pilots at least one warning device 50, 51, 52, in order to generate a specific emission pattern of at least one warning signal, called receipt-acknowledgement pattern MOA, which will be understood by the first wearer as meaning that at least one addressee of his request has properly received and understood his request, and has acknowledged the receipt of the latter, possibly accompanied with instructions and/or information.

A processing of the different receipt-acknowledgement messages MAR is done in order to avoid the first wearer receiving several receipt-acknowledgement messages MAR for the same message MES, this processing applying on the receipt-acknowledgement messages MAR both with and without instructions and/or information.

Figure 5:
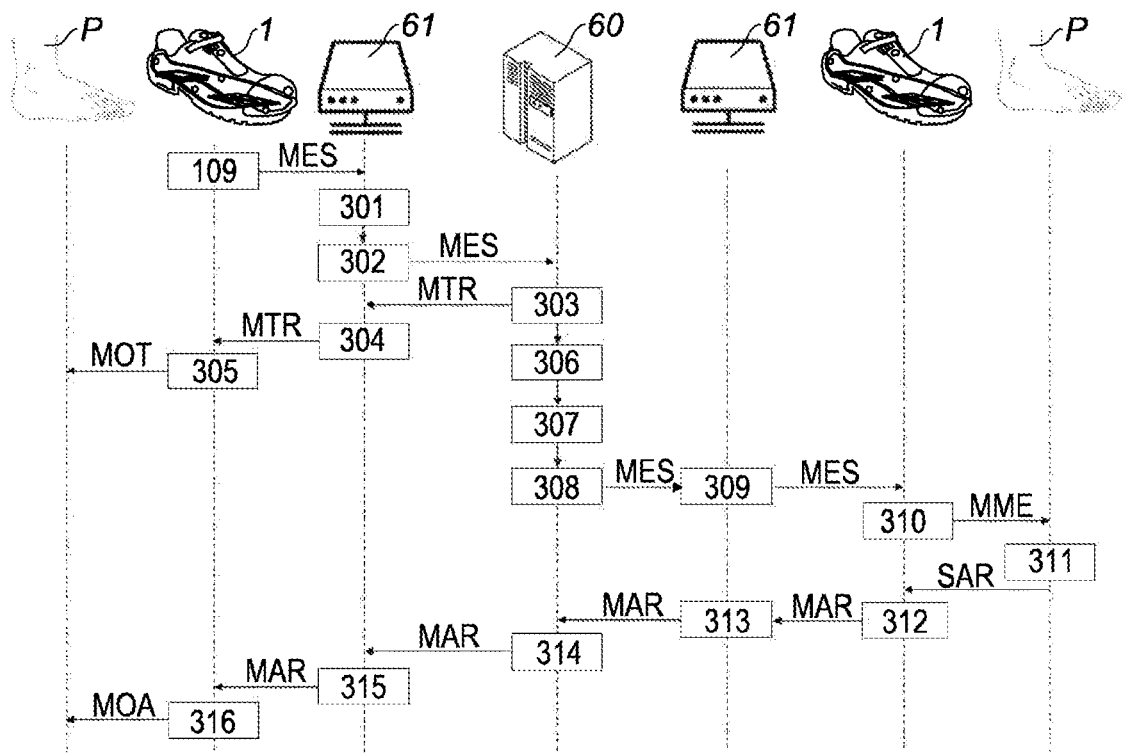
FIG. 5 is a flowchart of a third phase of communication, which follows the first phase of FIG. 3, between the first shoe and a remote second shoe via the first gateway, a central server, and a second gateway in accordance with the present disclosure.

Referring to FIG. 5, a third communication phase, which follows the first communication phase described hereinabove with reference to FIG. 3, consists of a communication between the first wearer whose foot P is in the first shoe 1, the first shoe 1, the first gateway 61, the central server 60, a second gateway 61, a second wearer whose foot P is in a second shoe 1 and the second shoe 1, and is described hereinafter. In this third phase, the second shoe 1 is not within the reach of the first gateway 61 on the LPWAN or LTN network, and is therefore accessible only via the central server 60 and via a second gateway 61 which is within the reach of the second shoe 1.

After reception of the message MES coming from the first shoe 1, at a first step 301, the first gateway 61 checks up thanks to a local database whether other shoes 1 (and therefore other wearers) are within reach for receiving the message MES. In this instance, all the shoes 1 having to receive the message MES are not within reach.

At a second step 302, the first gateway 61 having not detected that all the shoes 1 having to receive the message MES are within reach, it redirects the message MES to the central server 60. It goes without saying that this third phase may be performed in parallel with the second phase, so that the shoes 1 within the reach of the first gateway 61 as well as the shoes 1 that are not within the reach of the first gateway 61 could receive the request of the first wearer.

At a third step 303, the central server 60 receives the message MES and transmits to the first gateway 61 a processing message MTR meaning that it is processing the request of the first wearer.

At a fourth step 304, the first gateway 61 redirects the processing message MTR to the first shoe 1 within reach.

At a fifth step 305, the digital processing center 20 of the first shoe 1 receives the processing message MTR and then pilots at least one warning device 50, 51, 52, in order to generate a specific emission pattern of at least one warning signal, called processing pattern MOT, which will be understood by the first wearer as meaning that his request has been properly received and is being processed.

At a sixth step 306, the central server 60 checks up whether management options have been set by a manager of the installation 6 regarding the redirection of the message MES to either external service (e.g., a public utility service, a safety officer, a direct supervisor), and checks up in particular whether an approval from a rank 1 officer (for example the manager or a direct supervisor) should be obtained before redirecting the message MES. In this case, an exchange is set up between the rank 1 officer and the central server 60 in order to gather his approval.

Among these management options, there is also the possibility to require the approval of a rank 2 officer if the rank 1 officer has not responded within a given time frame, and so on with a rank 3 officer, etc.

At a seventh step 307, if the approval of an officer is received or if such an approval is not needed in the management options, then the central server 60 looks up which final addressee (eg. another wearer, a public utility service, an officer, . . . ) of the installation 6 should be informed about the request of the first wearer.

During this research, there may be provided a filter for selecting the final addressee(s) (eg. another wearer, a public utility service, . . . ) of the message MES, this filter may be automated (depending on the type or content of the message MES) and/or may be manual and thus be expressed by the officer who gives his approval.

In this third phase, the final addressee is a second wearer, bearing in mind that it may also consist of a public utility service (see the fourth communication phase described hereinafter with reference to FIG. 6).

At an eight step 308, the central server 60 having detected a second wearer accessible via a second gateway 61, the central server 60 redirects the message MES to the second gateway 61.

Afterwards, steps 309 to 312 substantially correspond to the previously-described steps 202 to 205, where at the end of the twelfth step 312, the digital processing center 20 of the second shoe 1 transmits the receipt-acknowledgement message MAR to the second gateway 61.

During steps 313 to 315, the receipt-acknowledgement message MAR is redirected to the first shoe 1 via the second gateway 61, the central server 60 and the first gateway 61, and the sixteenth step 316 substantially corresponds to step 207 with the generation of the receipt-acknowledgement pattern MOA.

Figure 6:
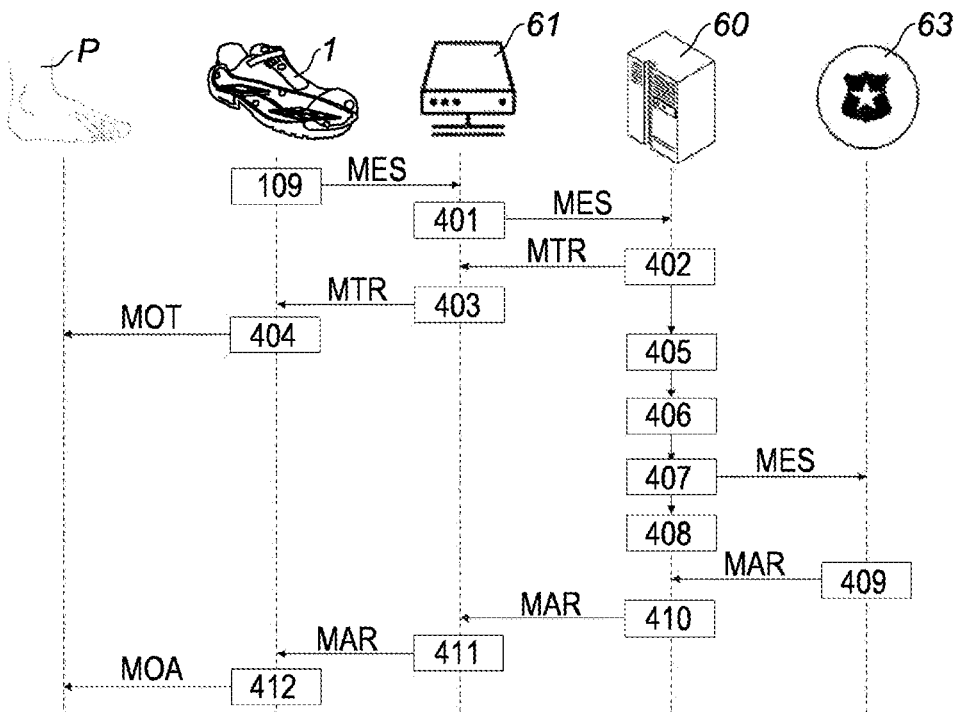
FIG. 6 is a flowchart of a fourth phase of communication, which follows the first phase of FIG. 3, between the first shoe and a public utility service (such as the fire department, the police, the healthcare, etc) via the first gateway and the central server in accordance with the present disclosure.

Referring to FIG. 6, a fourth communication phase, which follows the first communication phase described hereinabove with reference to FIG. 3, consists of a communication between the first wearer whose foot P is in the first shoe 1, the first shoe 1, the first gateway 61, the central server 60 and a public utility service server 63.

After reception of the message MES coming from the first shoe 1, at a first step 401, the first gateway 61 redirects the message MES to the central server 60. Of course, step 301 could have been present, bearing in mind that this fourth phase may proceed in parallel with the third phase and/or with the second phase.

Steps 402 to 405 substantially correspond to the previously-described steps 303 to 306.

The sixth step 406 substantially corresponds to step 307, with the difference that the selected final addressee is a public utility service server 63, in the context of this fourth communication phase.

At a seventh step 407, the central server 60 redirects the message MES to the public utility service server 63 and, at an eighth step 408, the central server 60 records the sending of this message MES to the public utility service server 63. The message MES may be formatted beforehand so as to fit in at best into the information system of the public utility service 63.

At a ninth step 409, the public utility service server 63 receives the message MES and returns to the central server 60 a receipt-acknowledgement message MAR, which may possibly contain instructions and/or information intended to the first wearer.

During steps 410 and 411, the receipt-acknowledgement message MAR is redirected to the first shoe 1 via the central server 60 and the first gateway 61, and the twelfth step 412 substantially corresponds to step 207 with the generation of the receipt-acknowledgement pattern MOA.

Figure 7:
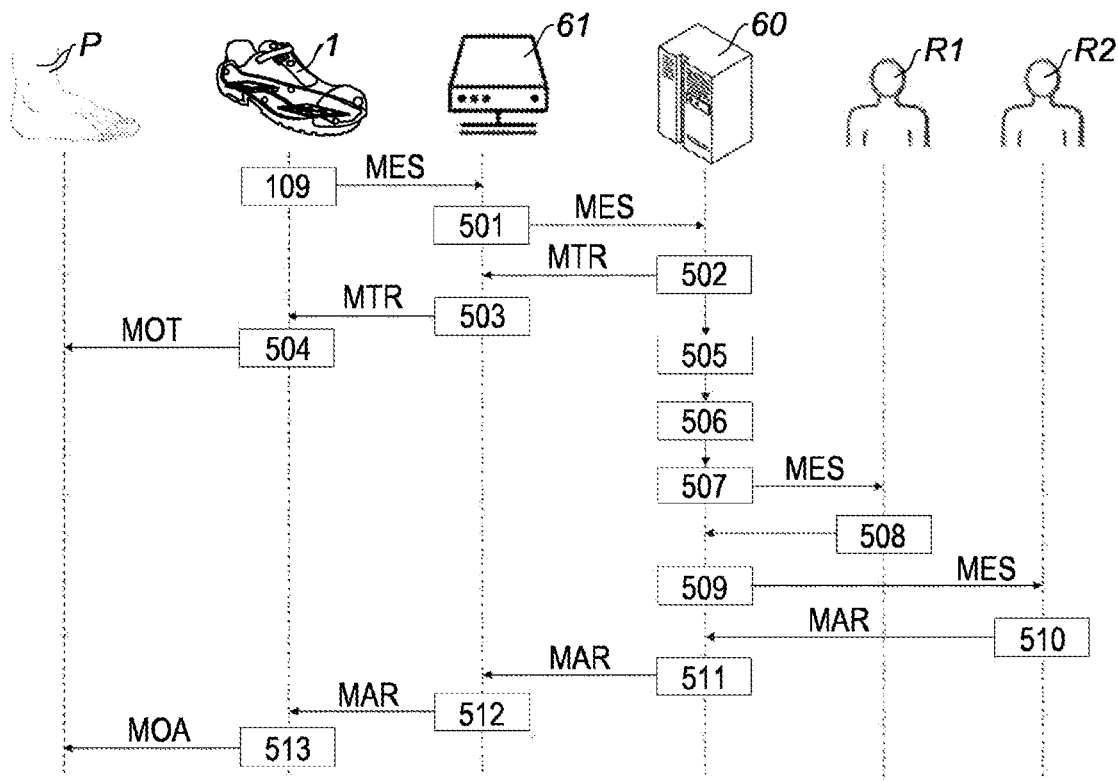
FIG. 7 is a flowchart of a fifth phase of communication, which follows the first phase of FIG. 3, between the first shoe and persons (such as a direct supervisor or a safety actor) via the first gateway and the central server in accordance with the present disclosure.

Referring to FIG. 7, a fifth communication phase, which follows the first communication phase described hereinabove with reference to FIG. 3, consists of a communication between the first wearer whose foot P is in the first shoe 1, the first shoe 1, the first gateway 61, the central server 60 and one or several officer(s) R1, R2, such as the direct officers, managers, safety officers.

After reception of the message MES coming from the first shoe 1, at a first step 501, the first gateway 61 redirects the message MES to the central server 60. Of course, step 301 could have been present, bearing in mind that this fifth phase may proceed in parallel with the second, third and/or fourth phases.

Steps 502 to 505 substantially correspond to the previously-described steps 303 to 306.

The sixth step 506 substantially corresponds to step 307, with the difference that the selected final addressee is an officer R1, in the context of this fifth communication phase. It may consist of a safety officer or of a direct officer present (or not) on the site where stands the first wearer.

At a seventh step 507, the central server 60 having detected an officer R1, the central server 60 redirects the message MES to this officer R1, who may receive it via a shoe 1 (and we return to the previously-described second and third communication phases), a mobile application, a text or voice message on the mobile or computer terminal.

At an eighth step 508, the officer R1 receives the message MES and returns to the central server 60 a receipt-acknowledgement message MAR, which may possibly contain instructions and/or information intended to the first wearer.

In the absence of reception of the receipt-acknowledgement message MAR from the officer R1 (for example after sending several of the message MES and/or after a given time frame), at a ninth step 509, the central server 60 looks up for another officer R2 and redirects the message MES to this other officer R2, who should, in turn, return a receipt-acknowledgement message MAR at a tenth step 510.

During steps 511 and 512, the receipt-acknowledgement message MAR is redirected to the first shoe 1 via the central server 60 and the first gateway 61, and the thirteenth step 513 substantially corresponds to step 207 with the generation of the receipt-acknowledgement pattern MOA.

Figure 8:
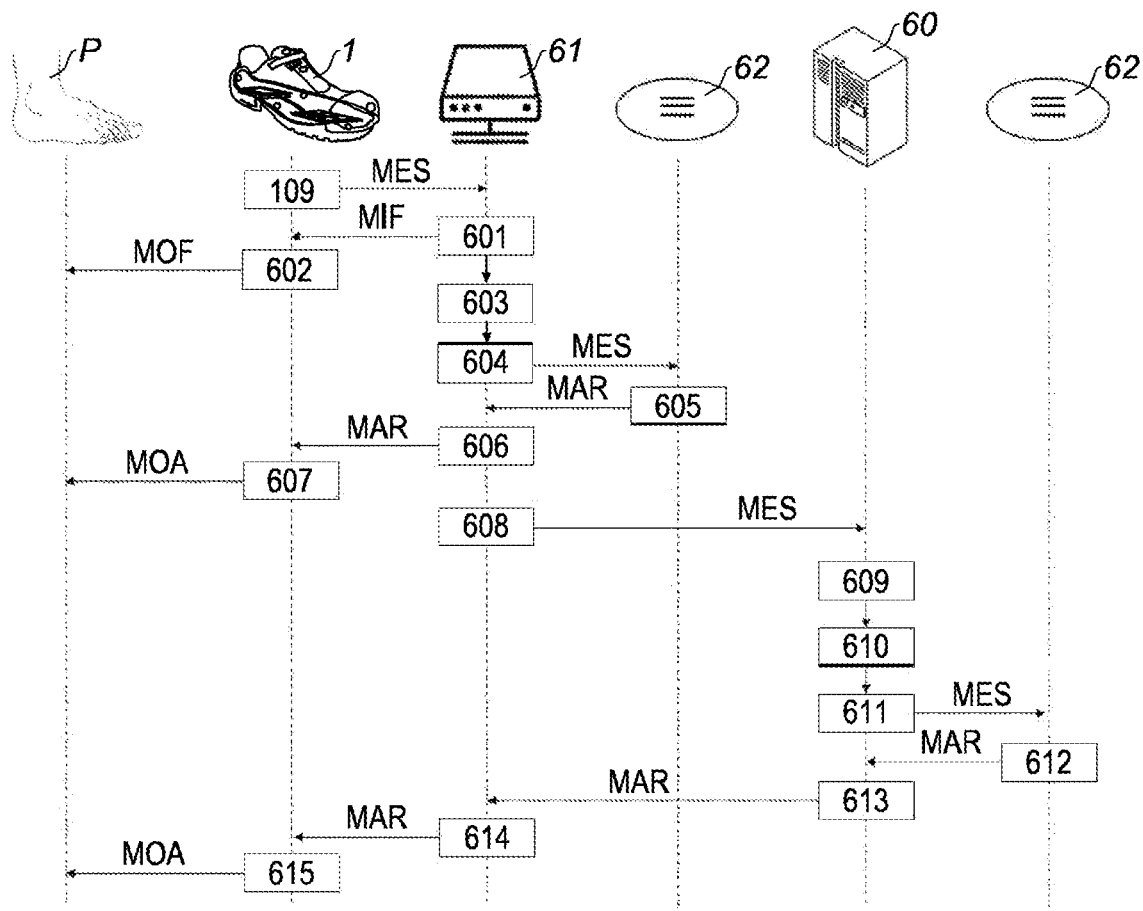
FIG. 8 is a flowchart of a sixth phase of communication, which follows the first phase of FIG. 3, between the first shoe and a first connected apparatus via the first gateway, and between the first shoe and a second connected apparatus via the first gateway and the central server in accordance with the present disclosure.

Referring to FIG. 8, a sixth communication phase, which follows the first communication phase described hereinabove with reference to FIG. 3, consists of a communication between the first wearer whose foot P is in the first shoe 1, the first shoe 1, the first gateway 61, a local first connected apparatus 62 accessible via the first gateway 61 or a remote second connected apparatus 62 accessible via the central server 60.

After reception of the message MES coming from the first shoe 1, at a first step 601, the first gateway 61 analyzes the messages MES that it interprets as having to be transmitted in priority to a connected apparatus 62 (for example a siren, a gas aspiration, etc.), and it addresses an information message MIF in order to inform the first wearer that his message is being processed.

At a second step 602, the digital processing center 20 of the first shoe 1 receives the information message MIF and then pilots at least one warning device 50, 51, 52, in order to generate a specific emission pattern of at least one warning signal, called information pattern MOF, which will be understood by the first wearer as meaning that his message is being processed.

At a third step 603, the first gateway 61 checks up, in a local database, whether connected apparatuses 62 intended to receive the message MES are within reach on a LPWAN or LTN network, for a rapid processing of the message.

At a fourth step 604, having detected a first connected apparatus 62 on its LPWAN or LTN network, the first gateway 61 redirects the message MES to the first connected apparatus 62.

At a fifth step 605, the first connected apparatus 62 receives the message MES and returns to the first gateway 61 a receipt-acknowledgement message MAR, and steps 606 and 607 substantially correspond to steps 206 and 207.

At an eight step 608, having not detected any connected apparatus 62 on its LPWAN or LTN network, the first gateway 61 redirects the message MES to the central server 60.

At a ninth step 609, the central server 60 checks up whether management options have been set by a manager of the installation 6 regarding the redirection of the message MES to either connected apparatus 62, in the same manner as at step 306, and checks up in particular whether an approval of an officer should be obtained before redirecting the message MES.

At a tenth step 610, if the approval of an officer is received or if such an approval is not needed in the management options, then the central server 60 looks up which connected apparatus 62 of the installation 6 should be informed about the request of the first wearer, for example depending on the content of the message MES, or still on a relationship between the first wearer and the connected apparatus 62 (team relationship, company relationship, . . . ).

At an eleventh step 611, the central server 60 having detected a second connected apparatus 62 to be informed, the central server 60 redirects the message MES to this second connected apparatus 62 (either directly or via a second gateway 61).

At a twelfth step 612, the second connected apparatus 62 receives the message MES and returns to the central server 60 a receipt-acknowledgement message MAR.

During steps 613 and 614, the receipt-acknowledgement message MAR is redirected to the first shoe 1 via the central server 60 and the first gateway 61, and the fifteenth step 615 substantially corresponds to step 207 with the generation of the receipt-acknowledgement pattern MOA.

In the following seventh and eighth communication phases, the communication concerns a central server 60 or a connected apparatus 62 or a public utility service 63 and one or several actor(s) of the installation 6. For example, referring to FIG. 9, the communication phase takes place between a central server 60 and one or several shoe 1 wearer(s) via one or several gateway(s) 61. For clarity reasons, the seventh and eighth communication phases listed below will concern the communication between a first wearer of a first shoe 1 and a central server 60 (seventh communication phase of FIG. 9) or a connected apparatus 62 (eighth communication phase of FIG. 10); but these communication phases remain valid in the case of other actors of the installation 6 or several actors of the installation 6.

Figure 9:
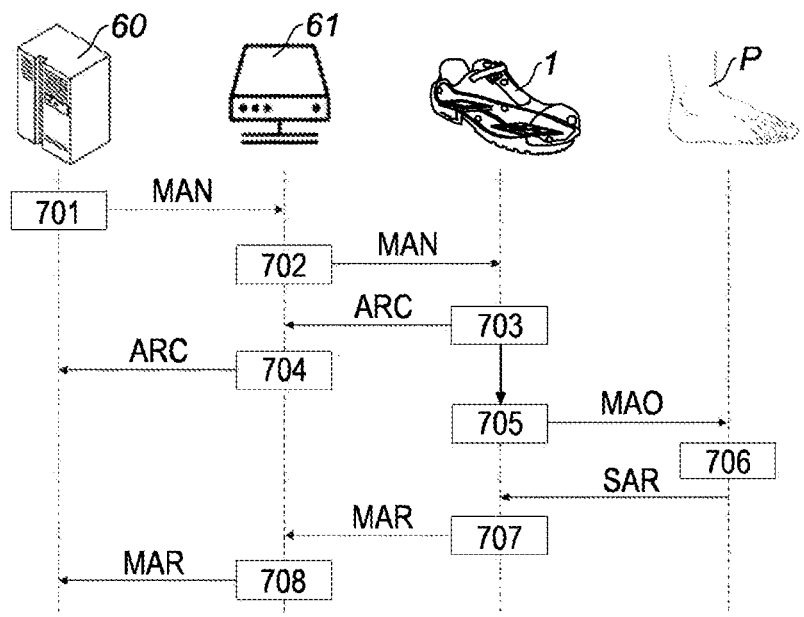
FIG. 9 is a flowchart of a seventh phase of communication between the central server and the first shoe via the first gateway in accordance with the present disclosure.

Referring to FIG. 9, a seventh communication phases consists of a communication between the central server 60 and the wearer of the first shoe 1 via the first gateway 61.

At a first step 701, the central server 60 transmits an announcement message MAN to the first gateway 61, this announcement message MAN being intended to the wearer of the first shoe 1 which is in connection on the LPWAN or LTN network with the first gateway 61.

This announcement message MAN may have been edited by a manager or another officer, for example by means of an interface such as a computer terminal or mobile terminal, in order to address information and/or instructions, bearing in mind that this announcement message MAN may be intended to other shoes 1 wearers.

At a second step 702, the first gateway 61 having detected the first shoe 1 within reach, it redirects the announcement message MAN to the first shoe 1.

At a third step 703, the digital processing center 20 of the first shoe 1 receives the announcement message MAN and returns to the first gateway 61 a shoe receipt-acknowledgement message ARC which indicates that the first shoe 1 has properly received the announcement message MAN.

At a fourth step 704, the first gateway 61 redirects the shoe receipt-acknowledgement message ARC to the central server 60.

At a fifth step 705, after reception of the announcement message MAN, the digital processing center 20 of the first shoe 1 pilots at least one warning device 50, 51, 52, in order to generate a specific emission pattern of at least one warning signal, called announcement pattern MAO, which will be understood by the first wearer by associating it to the announcement message MAN addressed by the central server 60. In other words, the first wearer receives this announcement pattern MAO in his first shoe 1, and knows how to translate it into an intelligible information and/or instruction.

In order to attract the attention of the first wearer, the announcement pattern MAO may be preceded by a wake-up pattern (for example a long vibration followed by a break) so that the first wearer could concentrate on the announcement pattern MAO that follows.

At a sixth step 706, the first wearer, having understood the information and/or instruction, confirms the proper reception and the proper understanding of the announcement pattern MAO by performing with his foot P a sequence of successive efforts on the force sensor(s) 4 which corresponds to a receipt-acknowledgement haptic sequence SAR. As long as the first wearer has not performed the receipt-acknowledgement haptic sequence SAR, the announcement message pattern MAO is repeated at regular intervals on his first shoe 1. It should be noted that this receipt-acknowledgement haptic sequence SAR may also contain a specific sub-sequence SSI relating to instructions and/or information intended to the central server 60.

At a seventh step 707, the digital processing center 20 of the first shoe 1 receives a detection signal SDAR of the receipt-acknowledgement haptic sequence SAR (after pre-processing and filtering of the measurement data of the force sensor(s) 4), and converts it into a receipt-acknowledgement message MAR, before transmitting it to the first gateway 61. At an eighth step 708, the first gateway 61 redirects the receipt-acknowledgement message MAR to the central server 60.

Figure 10:
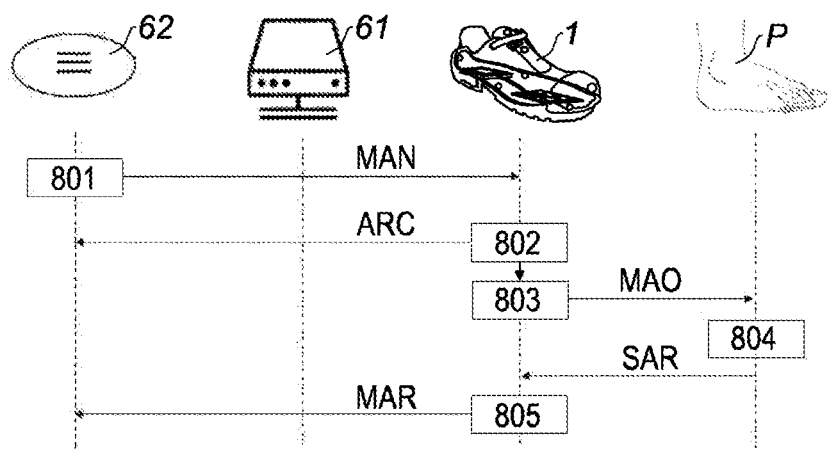
FIG. 10 is a flowchart of an eighth phase of communication between a connected apparatus and the first shoe in accordance with the present disclosure.

Referring to FIG. 10, an eighth communication phase consists of a communication between a connected apparatus 62 (and yet still a public utility service 63 although not illustrated) and the wearer of the first shoe 1.

At a first step 801, the connected apparatus 62 (or a public utility service 63) transmits an announcement message MAN to the first shoe 1 which is located within its reach in a LPWAN or LTN network, this announcement message MAN being intended to the wearer(s) for example in order to transmit a specific alert to the connected apparatus 62 (or public utility service 63) such as: «detection of a dangerous gas» if the connected apparatus is a gas detector, or «internal dysfunction, keep yourself away», or «you are too close from a danger area».

Steps 802 to 805 substantially correspond to the above-described steps 703 to 707, with the difference that, at the third step 703 and at the fifth step 805, the shoe receipt-acknowledgement message ARC and the receipt-acknowledgement message MAR are transmitted to the connected apparatus 62 (or to the public utility service 63).

In a non-illustrated variant, the different messages MAN, ARC and MAR may transit via a first gateway 61 if the first shoe 61 is not accessible by the connected apparatus on a LPWAN or LTN network.

In general, and in particular for the implementation of the above-described seventh and eighth phases, with reference to FIGS. 9 and 10, it is obvious that the digital processing center 20 of the shoe 1 is in a listening phase in order to receive any entering message, and in particular the announcement message MAN, without having the shoe 1 previously emit a message to the outside.

According to a first form, the digital processing center 20 of the shoe 1 is in a continuous listening phase, with neither interruption nor break, that is to say that the digital processing center 20 continuously opens at least one entering communication channel for the reception of any entering message that is addressed thereto from the outside. In this first form, the listening is called synchronous, to the extent that the reception of the entering message by the digital processing center 20 is synchronized on the emission of the entering message by the external emitter (person or machine), consideration being made to the radio-communication time delays.

According to a second form, the digital processing center 20 of the shoe 1 switches successively between:

listening phases during which the digital processing center 20 opens at least one entering communication channel for the reception of any entering message that is addressed thereto from the outside;

break phases during which the digital processing center 20 closes its or all its entering communication channel(s), mainly for energy saving reasons.

The durations of the listening phases and of the break phases are parameterizable, for example the break phases may last between 1 and 10 minutes, and even longer, depending on the context of the wearer of the shoe 1 and depending on the capacities of the battery 3.

In this second form, the digital processing center 20 receives the entering messages according to a desynchronized or asynchronous protocol as follows:

during the break phases, any entering message addressed from the outside is directed and stored in a messaging memory of a remote server, such as for example the central server 60 or another server dedicated to this task; and during the listening phases, the digital processing center 20 establishes a connection with this messaging memory and relays the stored entering message(s).

In this second form, the listening is called asynchronous, to the extent that the reception of the entering message by the digital processing center 20 is desynchronized relative to the emission of the entering message by the external emitter (person or machine).

Thus, throughout the different communication phases, it is obvious that a bidirectional, intelligible and complex communication may be established between the wearer of a shoe 1 and different external services, such as a central server 60, physical persons, a public utility service server, a connected apparatus, . . . .

By exploiting the force sensor(s) 4 and the vibrator(s) of the shoe 1, it is possible to communicate, discreetly, in a bidirectional and haptic manner with the wearer of the shoe 1.

It should be noted that the present disclosure may find application in fields other than that relating to safety or alert surveillance, such as for example:

communication solution for a person with disability by exploiting a garment accessory integrating at least one force sensor on which a portion of the body of this person may act (depending on the disability), or a haptic interface solution for video games, by using for example a glove as a garment accessory;

sensorial interaction solution for stimulating sensitive parts of the human body between two remote adults, by using for example an underwear as a garment accessory.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A garment item comprising:
    at least one bidirectional radio-communication module configured to emit and receive signals;
    at least one force sensor configured to detect an effort applied by a wearer of the garment item on the at least one force sensor;
    at least one warning device configured to emit a warning signal;
    at least one electric battery; and
    a digital processing center configured to be reprogrammable and is connected to the at least one bidirectional radio-communication module, to the at least one force sensor, to the at least one warning device, and to the electric battery, wherein:
    the digital processing center integrates a first conversion table and a second conversion table, the first conversion table is configured to convert a plurality of predefined sequences of successive efforts applied by the wearer on the force sensor to respective meaningful signals associated to a plurality of messages and the second conversion table is configured to convert one or more predefined external signals to respective emission patterns of at least one warning signal,
    the digital processing center is configured to pilot the at least one bidirectional radio-communication module to emit a meaningful signal, in response to the detection of at least one sequence of successive efforts on the force sensor from among the predefined sequences of successive efforts and to the conversion of the at least one sequence of successive efforts to the meaningful signal based on the first conversion table; and
    the digital processing center is configured to pilot the at least one warning device to emit the warning signal in response to the reception of an external signal by the at least one bidirectional radio-communication module and to the conversion of the external signal to the warning signal based on the second conversion table.

2. The garment item according to claim 1, wherein the at least one warning device includes a vibrator type device that is placed inside the garment item to emit a vibrational warning signal.

3. The garment item according to claim 1, wherein the at least one warning device includes at least one of a light source type device, a sound source type device, odorous source type device, or a combination thereof, wherein the light source type device is placed outside the garment item and operable to emit a luminous warning signal visible by at least the wearer, the sound source type device is operable to emit an audible warning signal audible by at least the wearer, and the odorous source type device is operable to emit an olfactive warning signal smelt by at least the wearer.

4. The garment item according to claim 1, wherein the garment item is a shoe comprising a sole and an upper stocking portion provided with an entrance for the introduction of a foot of a wearer.

5. The garment item according to claim 4, wherein the force sensor is positioned on an inner face of the upper stocking portion and at a front part of the shoe, such that the force sensor is placed above at least one toe of the foot.

6. The garment item according to claim 5 further comprising a safety shell placed at the front part of the shoe, wherein the force sensor is disposed beneath said safety shell.

7. The garment item according to claim 4 further comprising a detector connected to the digital processing center, and operable to detect the presence of the foot inside the shoe.

8. The garment item according claim 1, wherein the digital processing center switches successively between:
    a listening phase during which the digital processing center opens at least one entering communication channel for the reception of an entering message that is addressed thereto from the outside, and
    a break phase during which the digital processing center closes one or more of the at least one entering communication channel.

9. The garment item according to claim 1, wherein the at least one bidirectional radio-communication module includes a long-range radio-communication chip according to at least one of a low power wide area network (LPWAN) and a low throughput network (LPN).

10. The garment item according to claim 1, wherein the at least one bidirectional radio-communication module includes a short-range radio-communication chip according to at least one of a wireless body area network (WBAN) and wireless body area sensor network (WBASN) to establish a radio-communication link between the garment item and at least one portable device carried by the wearer.

11. An installation for bidirectional communication with at least one wearer of a garment item in accordance with claim 1, the installation comprising a garment item according to claim 1, a remote central server and at least one gateway for connection between a bidirectional radio-communication module of the garment item and the central server.

12. The installation according to claim 11 further comprising at least one other garment item according to claim 1, and wherein the bidirectional radio-communication module of the garment item is communicably coupled to a bidirectional radio-communication module of the other garment item, either directly or via a gateway.

13. The installation according to claim 12 further comprising several garment items according to claim 1, and wherein the bidirectional radio-communication modules of the several garment items form a mesh local area network whose nodes are the bidirectional radio-communication modules that are connected with at least part of each other in a decentralized manner.

14. The installation according to claim 11 further comprising at least one connected apparatus equipped with at least one sensor for measuring a parameter or at least one actuator, the connected apparatus further comprising a bidirectional radio-communication module configured to emit measurement data of the at least one sensor or receive piloting data of the at least one actuator, and wherein the bidirectional radio-communication module of the garment item is in connection with the bidirectional radio-communication module of the at least one connected apparatus, either directly or via the gateway.

15. The installation according to claim 14 further comprising:
    at least one portable device carried by the wearer of the garment item, wherein the at least one portable device includes at least one sensor for measuring a parameter, or at least one actuator and warning device, and the at least one portable device further includes at least one short-range radio-communication chip according to at least one of wireless body area network (WBAN) and wireless body area sensor network (WBASN), and wherein the at least one bidirectional radio-communication module of the garment includes a short-range radio-communication chip according to at least one of a WBAN and WBASN to establish a radio-communication link between the garment item and the at least one portable device carried by the wearer.

16. A bidirectional communication method for a bidirectional communication with a garment item according to claim 1, the method comprising the following steps:
   detection of a sequence of successive efforts performed by a wearer of the garment item on the at least one force sensor;
   reception by the digital processing center of a detection signal of the sequence of successive efforts by the at least one force sensor;
   analysis by the digital processing center of said detection signal in order to check up whether it is associated to a predefined meaningful signal corresponding to an intelligible message;
   conversion by the first conversion table of the sequence of successive efforts applied by the wearer on the force sensor to a meaningful signal associated to the intelligible message;
   piloting by the digital processing center of the at least one warning device so as to emit a warning signal in response to the reception of the detection signal;
   piloting by the digital processing center of the bidirectional radio-communication module to emit the meaningful signal;
   reception of an external signal by the bidirectional radio-communication module;
   transmission of the external signal to the digital processing center;
   conversion by the second conversion table of the external signal to an emission pattern of at least one warning signal; and
   piloting by the digital processing center of the at least one warning device to emit the warning signal in response to the reception of the external signal.

17. The bidirectional communication method according to claim 16, wherein the digital processing center switches successively between:
   a listening phase during which the digital processing center opens at least one entering communication channel for the reception of any entering message that is addressed thereto from the outside, and
   a break phase during which the digital processing center closes one or more of the at least one entering communication channel.

18. The bidirectional communication method according to claim 17 further comprising the following successive steps:
   during the listening phase, the digital processing center receives an announcement message coming from an external emitter;
   the digital processing center pilots at least one warning device to generate a specific emission announcement pattern of at least one warning signal;
   the digital processing center receives a detection signal originating from the at least one force sensor in response to the completion, by the wearer of the garment item, of a sequence of successive efforts on the at least one force sensor and which corresponds to a receipt-acknowledgement haptic sequence;
   the digital processing center converts the detection signal into a receipt-acknowledgement message; and
   the digital processing center communicates the receipt-acknowledgement message to the external emitter.

* * * * *